(12) United States Patent
Kohara et al.

(10) Patent No.: US 10,160,979 B2
(45) Date of Patent: Dec. 25, 2018

(54) PHARMACEUTICAL COMPOSITION FOR TREATMENT AND/OR PREVENTION OF HEPATITIS C

(71) Applicants: TOKYO METROPOLITAN INSTITUTE OF MEDICAL SCIENCE, Tokyo (JP); NATIONAL INSTITUTES OF BIOMEDICAL INNOVATION, HEALTH AND NUTRITION, Osaka (JP); THE CHEMO-SERO-THERAPEUTIC RESEARCH INSTITUTE, Kumamoto (JP)

(72) Inventors: Michinori Kohara, Tokyo (JP); Yasuhiro Yasutomi, Ibaraki (JP); Yumiko Shiogama, Ibaraki (JP)

(73) Assignees: Tokyo Metropolitan Institute of Medical Science, Tokyo (JP); National Institutes of Biomedical Innovation, Health and Nutrition, Osaka (JP); KM Biologics Co., Ltd., Kumamoto (JP)

( * ) Notice: Subject to any disclaimer, the term of this patent is extended or adjusted under 35 U.S.C. 154(b) by 0 days.

(21) Appl. No.: 15/524,879

(22) PCT Filed: Nov. 11, 2015

(86) PCT No.: PCT/JP2015/082327
§ 371 (c)(1),
(2) Date: May 5, 2017

(87) PCT Pub. No.: WO2016/076441
PCT Pub. Date: May 19, 2016

(65) Prior Publication Data
US 2017/0335345 A1 Nov. 23, 2017

(30) Foreign Application Priority Data

Nov. 11, 2014 (JP) ................. 2014-229283

(51) Int. Cl.
| | |
|---|---|
| A61K 39/00 | (2006.01) |
| A61K 39/12 | (2006.01) |
| A61K 39/275 | (2006.01) |
| A01N 63/00 | (2006.01) |
| A61K 48/00 | (2006.01) |
| C12N 15/863 | (2006.01) |
| A61K 39/29 | (2006.01) |
| A61K 31/7088 | (2006.01) |
| A61K 35/76 | (2015.01) |
| C12N 15/09 | (2006.01) |
| G01N 33/576 | (2006.01) |
| C07H 21/00 | (2006.01) |

(52) U.S. Cl.
CPC ...... *C12N 15/8636* (2013.01); *A61K 31/7088* (2013.01); *A61K 35/76* (2013.01); *A61K 39/29* (2013.01); *C12N 15/09* (2013.01); *G01N 33/5767* (2013.01); *A61K 48/00* (2013.01); *C07H 21/00* (2013.01)

(58) Field of Classification Search
CPC .... A61K 2039/5256; A61K 2039/5254; A61K 39/285; A61K 48/00; C12N 2710/24143
See application file for complete search history.

(56) References Cited

U.S. PATENT DOCUMENTS

2011/0275139 A1* 11/2011 Kohara .............. A01K 67/0275
435/235.1

FOREIGN PATENT DOCUMENTS

WO 2014/176530 A1 10/2014

OTHER PUBLICATIONS

Fournilllier et al., "A heterologous prime/boost vaccination strategy enhances the immunogenicity of therapeutic vaccines for hepatitis C virus", The Journal of Infectious Diseases, 2013, 208:1008-1019.*

Fournillier et al. "A heterologous prime/boost vaccination strategy enhances the immunogenicity of therapeutic vaccines for hepatitis C virus" (The Journal of Infectious Diseases, 2013, vol. 208:1008-1019.*

Anne Fournillier et al., "A Heterologous Prime/Boost Vaccination Strategy Enhances the Immunogenicity of Therapeutic Vaccines for Hepatitis C Virus," The Journal of Infectious Diseases, 2013, 208, 1008-19, ISSN 0022-1899.

Takeshi Wada et al., "DNA vaccine expressing the non-structural proteins of hepatitis C virus diminishes the expression of HCV proteins in a mouse model," Vaccine, 2013, 31, 5968-74, ISSN: 0264-410X.

Yao Deng et al., "Induction of Broadly Neutralising HCV Antibodies in Mice by Integration-Deficient Lentiviral Vector-Based Pseudotyped Particles," PLOS ONE, 2013, vol. 8, No. 4, e62684, 1-7, ISSN 1932-6203.

(Continued)

*Primary Examiner* — Barry A Chestnut
(74) *Attorney, Agent, or Firm* — McDermott Will & Emery LLP

(57) ABSTRACT

The present invention can induce stronger cellular immunity to hepatitis C and provide a treatment means and a prevention means that are effective in completely eliminating the hepatitis C virus (HCV). Provided is a pharmaceutical composition for the treatment and/or prevention of hepatitis C, said composition comprising a recombinant vaccinia virus (a) and a recombinant vector (b) and characterized in that after one of the recombinant vaccinia virus (a) and the recombinant vector (b) is administered for initial immunity, the other is administered for additional immunity. The recombinant vaccinia virus (a) contains an expression promoter and all or a portion of the cDNA of the HCV genome. The recombinant vector (b) contains an expression promoter and all or a portion of the cDNA of the HCV (where the cDNA contained in the recombinant vector (b) has a different base sequence than that included in the recombinant vaccinia virus (a)).

7 Claims, 10 Drawing Sheets
(10 of 10 Drawing Sheet(s) Filed in Color)
Specification includes a Sequence Listing.

(56) References Cited

OTHER PUBLICATIONS

Yukio Koide et al., "Control of infections by DNA Vaccine," Blood Immunity Cancer, 2002, vol. 7, No. 4, 372 to 384, ISSN:1341-5824. with partial English translation.

Yumiko Shiogama et al., "Investigation of Hepatitis Virus—Specific Immunostimulating Effect by Prime/Boost Method Using DNA Vaccine and Recombinant Vaccina Virus Against Hepatitis C Virus," The 18th Annual Meeting of the Japanese Society for Vaccinology, Dec. 6, 2014, vol. 18th, 127 with partial English translation.

Takaji Wakita et al., "Efficient Conditional Transgene Expression in Hepatitis C Virus cDNA Transgenic Mice Mediated by the Cre/loxP System," J. Biol. Chem., 1998, vol. 273, p. 9001-9006.

Kazuaki Inoue, et al., "Evaluation of a Cyclophilin Inhibitor in Hepatitis C Virus-Infected Chimeric Mice In Vivo," Hepatology, 2007, vol. 45, p. 921-928.

Q.L. Choo et al., "Vaccination of chimpanzees against infection by the hepatitis C virus," Pros. Natl. Acad. Sci. 1994, vol. 91, p. 1294-1298.

M. Puig et al., "Immunization of chimpanzees with an envelope protein-based vaccine enhance specific humoral and cellular immune responses that delap hepatitis C virus infection," Vaccine 2004, vol. 22, p. 991-1000.

J.D. Abraham et al., "Comparative immunogenicity analysis of modified vaccinia Ankara vectors expressing native or modified forms of hepatitis C virus E1 and E2 glycoproteins," Vaccine 2004, vol. 22, p. 3917-3928.

G.A. Elmowalid et. al., "Immunization with hepatitis C virus-like particles results in control of hepatitis C virus infection in chimpanzees," Pros. Natl. Acad. Sci. 2007, vol. 104, p. 8427-8432.

M. Houghton, "Prospects for prophylactic and therapeutic vaccines against the hepatitis C viruses," Immunol. Rev., Jan. 2011, vol. 239(1), p. 99-108.

International Search Report issued in Application No. PCT/JP2014/082327 dated Feb. 16, 2016, with English translation.

Pancholi et al., "DNA Immunization with Hepatitis C Virus (HCV) Polycistronic Genes or Immunization by HCV DNA Priming—Recombinant Canarypox Virus Boosting Induces Immune Responses and Protection from Recombinant HCV-Vaccinia Virus Infection in HLA-A2.1-Transgenic Mice," Journal of Virology, vol. 77, No. 1, Jan. 2003, pp. 382-390.

Extended European Search Report issued in Application No. 15859816.9 dated Jul. 25, 2018.

* cited by examiner

PHARMACEUTICAL COMPOSITION FOR TREATMENT AND/OR PREVENTION OF HEPATITIS C

RELATED APPLICATIONS

This application is the U.S. National Phase under 35 U.S.C. § 371 of International Application No. PCT/JP2015/082327, filed on Nov. 11, 2015, which in turn claims the benefit of Japanese Application No. 2014-229283, filed on Nov. 11, 2014, the disclosures of which are incorporated by reference herein.

TECHNICAL FIELD

The present invention relates to a pharmaceutical composition for treating and/or preventing hepatitis C.

BACKGROUND ART

Two million people are suffering from hepatitis C virus (HCV) in Japan, among them 36,000 people develop hepatocellular carcinoma every year where many of said cancer patients result in death. Although interferon (IFN) is currently used as an anti-HCV drug, its effect is limited and associated with serious side effects. Therefore, there has been a need for the development of a safer and more effective drug. Moreover, urgent action is needed since the risk of developing cancer is increasing with the aging of the infected patients.

Under the current circumstances, drugs for suppressing replication of HCV virus such as nucleic acid analogs and protease inhibitors have been developed and used for the treatment. When these drugs are used for the treatment, however, a drug-resistant virus is likely to emerge and the action mechanism of the drugs suggests that complete elimination of the virus is difficult and thus lifelong medication is required. Recently, a highly active anti-HCV drug has been developed and used but the treatment cost thereof is very high as 800,000-1,200,000 yen per cycle, limiting the number of patients who can receive this treatment. Under such a circumstance, establishment of a safe and inexpensive curative treatment that allows withdrawal or release from lifelong medication has been strongly required.

The present inventors have established research resources relating to HCV research and established various model experimental systems by preparing infectious HCV cDNA clones and establishing infected animals such as transgenic mice and human liver chimeric mice that can develop hepatitis C (for example, see Non-patent document 1: Wakita T., et al., J. Biol. Chem., 1998, vol. 273, pp. 9001-9006). Major features of HCV infection include a high rate of persistent infection and transfer to development of chronic hepatitis. For a long period of time, the present inventors have devoted themselves to earnest analysis and research on this mechanism in terms of acquirement and deficit in immune tolerance using the above-described model experimental system and else (for example, see Non-patent document 2: Inoue K., et al., Hepatology, 2007, vol. 45, pp. 921-928).

Many attempts have been made so far to develop a vaccine for preventing HCV infection but there has been no achievement in completely preventing the infection (for example, see Non-patent document 3: Choo Q L., et al., Pros. Natl. Acad. Sci. 1994, vol. 91, pp. 1294-1298, Non-patent document 4: Puig M., et. al., Vaccine 2004, vol. 22, pp. 991-1000, Non-patent document 5: Abraham J D., Vaccine 2004, vol. 22, pp. 3917-3928 and Non-patent document 6: Elmowalid G A., et. al., Pros. Natl. Acad. Sci. 2007, vol. 104, pp. 8427-8432).

In general, a so-called prime-boost method is known in as a method for strongly inducing cell-mediated immunity, in which a primary immunization is performed with a DNA vaccine and then a boost immunization with a recombinant vaccinia virus (vaccinia vaccine) (for example, see Non-patent document 7: Houghton M., Immunol. Rev., 2011 January, vol. 239(1), p. 99-108).

SUMMARY OF THE INVENTION

Under such circumstances, development of treatment and prevention techniques that can induce stronger cell-mediated immunity against hepatitis C and that are effective in complete elimination of HCV has been desired.

The present invention was made considering such circumstances and provides a pharmaceutical composition for treating and/or preventing hepatitis C and else as described below.

(1) A pharmaceutical composition for treating and/or preventing hepatitis C, comprising a (a) recombinant vaccinia virus and a (b) recombinant vector below:

(a) a recombinant vaccinia virus comprising an expression promoter, and all or a part of cDNA of hepatitis C virus genome; and (b) a recombinant vector comprising an expression promoter, and all or a part of cDNA of hepatitis C virus genome (provided that it has a nucleotide sequence that differs from that of all or a part of cDNA of hepatitis C virus genome contained in the (a) recombinant vaccinia virus), wherein either one of the (a) recombinant vaccinia virus or the (b) recombinant vector is administered for a primary immunization, and then the other is administered for a boost immunization.

(2) A pharmaceutical composition for treating and/or preventing hepatitis C, comprising a (c) recombinant vaccinia virus and a (d) recombinant vaccinia virus below:

(c) a recombinant vaccinia virus comprising an expression promoter, and all or a part of cDNA of hepatitis C virus genome; and (d) a recombinant vaccinia virus comprising an expression promoter, and all or a part of cDNA of hepatitis C virus genome (provided that it has a nucleotide sequence that differs from that of all or a part of cDNA of hepatitis C virus genome contained in the (c) recombinant vaccinia virus), wherein either one of the (c) recombinant vaccinia virus or the (d) recombinant vaccinia virus is administered for a primary immunization, and then the other is administered for a boost immunization.

(3) The pharmaceutical composition according to (1) or (2) above, wherein the cDNAs of hepatitis C virus genome independently code for a structural protein of hepatitis C virus, a non-structural protein of hepatitis C virus, or a structural protein and a non-structural protein of hepatitis C virus.

(4) The pharmaceutical composition according to (1) or (2) above, wherein the cDNAs of hepatitis C virus genome are each independently any DNA of the following (a)-(f):

(a) DNA comprising the nucleotide sequence represented by SEQ ID NO:1;

(b) DNA that comprises a nucleotide sequence having 90% or more identity to DNA comprising the nucleotide sequence represented by SEQ ID NO:1 and that codes for a structural protein and a non-structural protein of hepatitis C virus;

(c) DNA comprising the nucleotide sequence represented by SEQ ID NO:2;

(d) DNA that comprises a nucleotide sequence having 90% or more identity to DNA comprising the nucleotide sequence represented by SEQ ID NO:2 and that codes for a structural protein and a non-structural protein of hepatitis C virus;

(e) DNA comprising the nucleotide sequence represented by SEQ ID NO:3; or (f) DNA that comprises a nucleotide sequence having 90% or more identity to DNA comprising the nucleotide sequence represented by SEQ ID NO:3 and that codes for a structural protein and a non-structural protein of hepatitis C virus.

(5) The pharmaceutical composition according to any one of (1) to (4) above, wherein the expression promoter is a hybrid promoter.

(6) The pharmaceutical composition according to (5) above, wherein the nucleotide sequence of the hybrid promoter is DNA of the following (a) or (b):

(a) DNA comprising the nucleotide sequence represented by SEQ ID NO:4; or (b) DNA that comprises a nucleotide sequence having 90% or more identity to DNA comprising the nucleotide sequence represented by SEQ ID NO:4 and that has promoter activity.

(7) The pharmaceutical composition according to any one of (1) to (6) above, wherein the vaccinia virus is strain LC16m8.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODES FOR CARRYING OUT THE INVENTION

Figure 1:
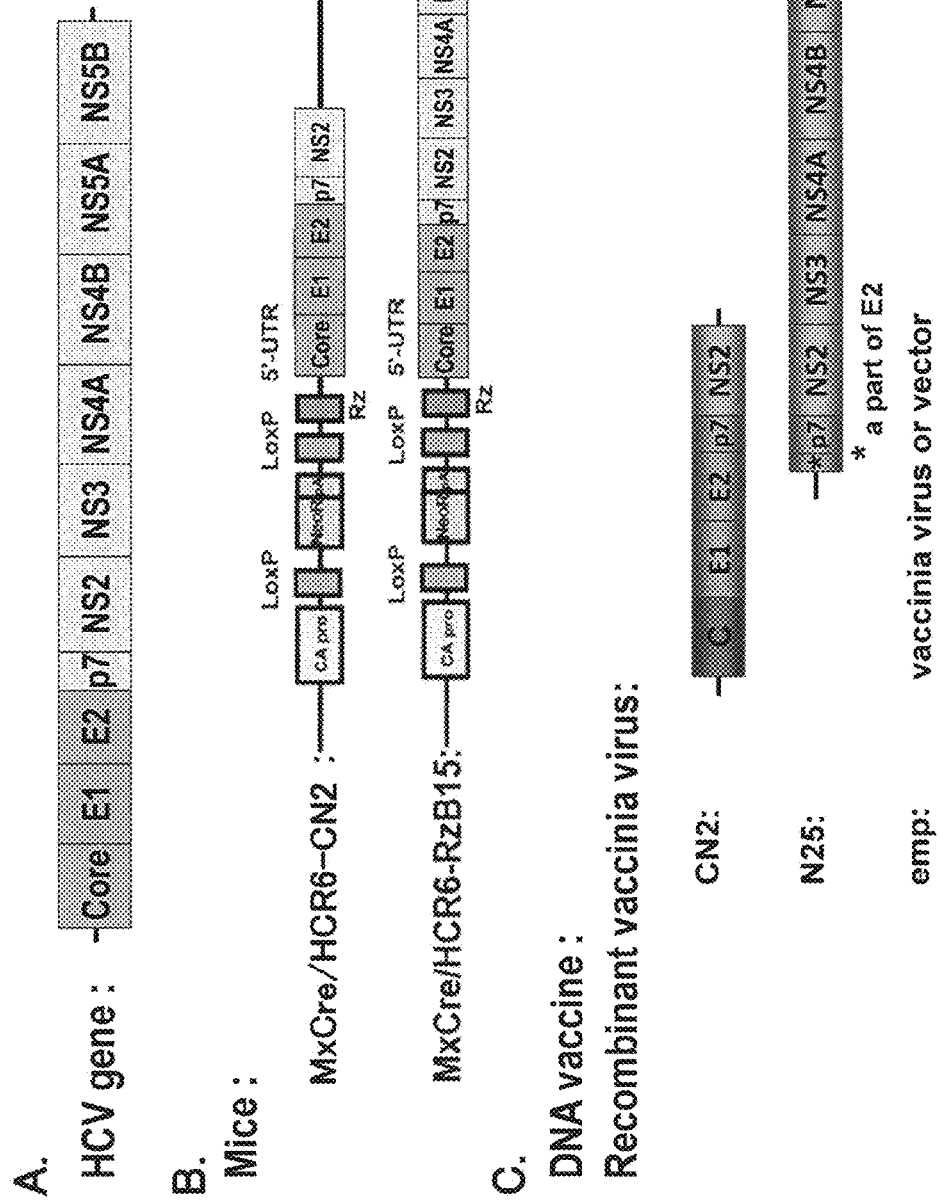
FIG. 1 is a diagram showing gene structures of hepatitis C model mice, a HCV gene expressing DNA vaccine and a recombinant vaccinia virus.

Hereinafter, the present invention will be described in detail. The scope of the present invention should not be limited to these descriptions and the present invention may appropriately be modified and carried out in a way apart from the following examples without departing from the spirit of the present invention.

The specification of Japanese Patent Application No. 2014-229283 (filed on Nov. 11, 2014) that serves as the basis of priority claimed by the present application is incorporated herein in its entirety. In addition, all of the references cited herein such as prior art documents, unexamined patent application publications, patent publications and other patent documents are incorporated herein by reference.

1. Summary of Invention

As described above, the present invention is a pharmaceutical composition for treating and/or preventing hepatitis C (hereinafter, also referred to as a "pharmaceutical composition of the present invention") comprising a (a) recombinant vaccinia virus below and a (b) recombinant vector, or a (c) recombinant vaccinia virus below and a (d) recombinant vaccinia virus below, wherein either one of the (a) recombinant vaccinia virus below or the (b) recombinant vector below is administered for a primary immunization and then the other for a boost immunization, or alternatively either one of the (c) recombinant vaccinia virus below or the (d) recombinant vaccinia virus below is administered for a primary immunization and then the other for a boost immunization. Here, (a), (c) and (d) below generally refers to so-called vaccinia vaccines while (b) below generally refers to a so-called DNA vaccine, but both are not particularly limited thereto:

(a) a recombinant vaccinia virus comprising an expression promoter, and all or a part of cDNA of hepatitis C virus genome;

(b) a recombinant vector comprising an expression promoter, and all or a part of cDNA of hepatitis C virus genome (provided that it has a nucleotide sequence that differs from that of all or a part of cDNA of hepatitis C virus genome contained in the (a) recombinant vaccinia virus);

(c) a recombinant vaccinia virus comprising an expression promoter, and all or a part of cDNA of hepatitis C virus genome;

(d) a recombinant vaccinia virus comprising an expression promoter, and all or a part of cDNA of hepatitis C virus genome (provided that it has a nucleotide sequence that differs from that of all or a part of cDNA of hepatitis C virus genome contained in the (c) recombinant vaccinia virus).

In order to induce cell-mediated immunity more strongly, a conventionally known prime-boost method generally employs a method for immunologically treating or preventing infectious disease or the like, in which a primary immunization is first conducted with a DNA vaccine which is followed by a boost immunization with a recombinant vaccinia virus (vaccinia vaccine) (previously cited Non-patent document 7, etc.). According to this conventionally known prime-boost method, it has been a technically common knowledge for those skilled in the art to use DNAs having substantially identical nucleotide sequences (to use DNAs from the same region of the genome cDNA) for DNA incorporated into a DNA vaccine used for a primary immunization (DNA derived from genome cDNA of causative virus or the like) as well as DNA incorporated into a recombinant vaccinia virus used for a boost immunization.

The present inventors, however, found that more significant and very strong specific cell-mediated immunity can be induced when DNAs having different nucleotide sequences (using DNAs from different regions of the genome cDNA of the causative virus or the like) are used as DNA incorporated into a vaccine for a primary immunization and DNA incorporated into a vaccine for a boost immunization, than when DNAs of the same region were used, which was totally unexpected before. They also found that this effect was more remarkable in a model animal (transgenic mouse) expressing full-length HCV gene that is less susceptible to immunostimulation. The present inventors further found that this remarkable effect can be achieved by using the DNA vaccine and the recombinant vaccinia virus (vaccinia vaccine) for the primary immunization and the boost immunization in either way, and also by using recombinant vaccinia viruses (vaccinia vaccines) for both of the primary immunization and the boost immunization, which has been totally unexpected in the conventional prime-boost methods. The present invention was accomplished based on these various findings achieved by keen and continuous experiments and research made by the present inventors.

2. Vaccinia Vaccine (Recombinant Vaccinia Virus)

The recombinant vaccinia viruses of (a), (c) and (d) mentioned in Item 1 above (namely, HCV recombinant vaccinia viruses; so-called vaccinia vaccines) and a method for preparing the same will be described below.

All of the genes coding for the protein of hepatitis C virus (HCV), the genes coding for the structural protein regions building the capsid and the genes coding for the non-structural protein regions involved in replication have already been cloned and inserted into plasmids. Therefore, genes contained in a recombinant vaccinia virus of the present invention can be obtained by a usual genetic engineering technique. For example, a nucleic acid synthesis method that uses a commonly used DNA synthesizer can be employed as the genetic engineering technique. Alternatively, a PCR technique in which a gene sequence is isolated and synthesized as a template and then primers specific to each gene are designed to amplify the gene sequence with a PCR equipment, or a gene amplification technique using a cloning vector may be employed. The above-described methods can easily be carried out by those skilled in the art with reference to "Molecular cloning, A Laboratory Manual 3rd ed." (Cold Spring Harbor Laboratory Press (2001)) or the like. The resulting PCR product can be purified by employing a known method.

According to a preferable embodiment of the present invention, the above-described HCV gene inserted into the plasmid (genotype 1b; Nucleic acid nos. 1-9611; DDBJ/EMBL/GenBank accession number; AY045702) can be used as a template. PCR can be carried out using cDNA of HCV gene as a template and primers specific to HCV gene to prepare each of the HCV gene regions. According to the present invention, all of the gene regions of HCV are referred to as "CN5", genes coding substantially for the structural protein regions of a structural protein building the capsid (partially including a gene coding for a non-structural protein region) are referred to as "CN2", and genes coding substantially for the non-structural protein regions involved in replication (partially including a gene coding for a structural protein region (specifically, a part of E2 region (but not full-length E2 region) and p7 region)) are referred to as "N25".

Nucleotide sequences of CN2, N25 and CN5 are represented by SEQ ID NOS:1, 2 and 3, respectively. Besides the DNA having the nucleotide sequences represented by SEQ ID NOS:1-3, the following DNAs can also be used in the present invention.

DNA that hybridizes with DNA having a nucleotide sequence complementary to the nucleotide sequence represented by SEQ ID NO:1 under stringent conditions and that codes for a structural protein and a non-structural protein of hepatitis C virus (DNA variant of CN2).

DNA that hybridizes with DNA having a nucleotide sequence complementary to the nucleotide sequence represented by SEQ ID NO:2 under stringent conditions and that codes for a structural protein and a non-structural protein of hepatitis C virus (DNA variant of N25).

DNA that hybridizes with DNA having a nucleotide sequence complementary to the nucleotide sequence represented by SEQ ID NO:3 under stringent conditions and that codes for a structural protein and a non-structural protein of hepatitis C virus (DNA variant of CN5).

Herein, the phrase "that codes for a structural protein of hepatitis C virus" means to code for a protein that builds the capsid of the virus, specifically, to code for at least the core region, the E1 region and the E2 region. In addition, the phrase "that codes for a non-structural protein of hepatitis C virus" means to code for a protein generated in the cell upon virus proliferation, specifically to code for at least the NS2 region, the NS3 region, the NS4a region, the NS4b region, the NS5a region and the NS5b region. Moreover, the phrase "that codes for a structural protein and a non-structural protein of hepatitis C virus" means to code for a protein that builds the capsid of the virus as well as a protein generated in the cell upon virus proliferation, specifically to code for at least the core region, the E1 region, the E2 region, the NS2 region, the NS3 region, the NS4a region, the NS4b region, the NS5a region and the NS5b region.

Moreover, the genes coding for the structural proteins and the genes coding for the non-structural proteins described above comprise full-length sequences as well as partial sequences thereof.

In the case of CN2, it does not has to be of a full length and may be a part thereof as long as it contains all or any of the core region, the E1 region, the E2 region, the p7 region and the NS2 region (or a part thereof). For example, the E1 region (589th-1164th) and the E2 region (1165th-2253rd) may be used among the nucleotide sequence represented by SEQ ID NO:1.

In the case of N25, it does not has to be of a full length and may be a part thereof as long as it contains all or any of the E2 region (specifically a part thereof), the p7 region, the NS2 region, the NS3 region, the NS4a region, the NS4b region, the NS5a region and the NS5b region. For example, the NS2 region (805th-1455th) and the NS3 region (1456th-3348th) may be used among the nucleotide sequence represented by SEQ ID NO:2.

In the case of CN5, it does not has to be of a full length and may be a part thereof as long as it contains all or any of the core region, the E1 region, the E2 region, the p7 region, the NS2 region, the NS3 region, the NS4a region, the NS4b region, the NS5a region and the NS5b region. For example, the E1 region (589th-1164th), the E2 region (1165th-2253rd), the NS2 region (2443rd-3093rd) and the NS3 region (3094th-4986th) may be used among the nucleotide sequence represented by SEQ ID NO:3.

The above-described DNA variants can be obtained by chemical synthesis, or from a cDNA library or a genome library by a known hybridization technique such as colony hybridization, plaque hybridization or Southern blotting using DNA having the nucleotide sequence represented by SEQ ID NOS:1-3 or a fragment thereof as a probe. Examples of the stringent conditions employed in the above-described hybridization include 0.1×SSC-10×SSC, 0.1%-1.0% SDS and 20° C.–80° C. More specifically, the conditions may include prehybridization at 37° C.-56° C. for 30 minutes or longer, followed by 1-3 times of washing in 0.1×SSC, 0.1% SDS at room temperature for 10-20 minutes. For a more detailed procedure of the hybridization technique, see "Molecular Cloning, A Laboratory Manual 3rd ed." (Cold Spring Harbor Press (2001)) or else.

Alternatively, DNA that has 50% or more, 60% or more, 70% or more, 80% or more, 90% or more, 95% or more, 98% or more or 99% or more homology (identity) with the nucleotide sequence represented by SEQ ID NO:1 and that codes for a structural protein and a non-structural protein of hepatitis C virus (DNA variant of CN2); DNA that has 50% or more, 60% or more, 70% or more, 80% or more, 90% or more, 95% or more, 98% or more or 99% or more homology (identity) with the nucleotide sequence represented by SEQ ID NO:2 and that codes for a structural protein and a non-structural protein of hepatitis C virus (DNA variant of N25); or DNA that has 50% or more, 60% or more, 70% or more, 80% or more, 90% or more, 95% or more, 98% or more or 99% or more homology (identity) with the nucleotide sequence represented by SEQ ID NO:3 and that codes for a non-structural protein and a structural protein of hepatitis C virus (DNA variant of CN5) may also be used.

A promoter contained in the recombinant vaccinia virus of the present invention is a hybrid promoter comprising a poxvirus A-type inclusion body (ATI) promoter and tandem repeats of 7.5 kDa vaccinia virus protein (p7.5) early expression promoter within the hemagglutinin (HA) gene region of vaccinia virus. This promoter can be linked to a suitable plasmid. For example, pBMSF7C is known (Arch. Virol. 138, 315-330, 1994; Japanese Unexamined Patent Application Publication No. Heisei 6-237773).

A nucleotide sequence of a hybrid promoter that can be used in the present invention is represented by SEQ ID NO:4. Other than DNA comprising the nucleotide sequence represented by SEQ ID NO:4, DNA that hybridizes to DNA having a nucleotide sequence complementary to the nucleotide sequence represented by SEQ ID NO:4 under stringent conditions and that has promoter activity can also be used in the present invention. The "stringent conditions" are the same as described above. The phrase "having promoter activity" means to have activity to initiate transcription of a gene coding for a structural protein or a non-structural protein. In addition, DNA that has 50% or more, 60% or more, 70% or more, 80% or more, 90% or more, 95% or more, 98% or more or 99% or more homology (identity) with the nucleotide sequence represented by SEQ ID NO:4 and that has promoter activity can also be used.

This hybrid promoter can express a large amount of protein in a completely glycosylated form from early to late vaccinia virus infection. According to the present invention, a plasmid vector having HCV gene (CN5) inserted downstream of the pBMSF7C promoter is referred to as pBMSF7C-CN5. In addition, according to the present invention, a plasmid vector substantially having a structural protein region (partially including a non-structural protein region) gene (CN2) inserted downstream of the pBMSF7C promoter is referred to pBMSF7C-CN2. Furthermore, a plasmid vector substantially having a non-structural protein region (partially including a structural protein region) gene (N25) inserted downstream of the pBMSF7C promoter is referred to as pBMSF7C-N25.

A recombinant vaccinia virus can be prepared by introducing these plasmid vectors into a host vaccinia virus. Any known technique can be employed to introduce the plasmid vector into a host. For example, each of the plasmid vectors pBMSF7C-CN5, pBMSF7C-CN2 and pBMSF7C-N25 can be introduced into an animal cell infected with attenuated vaccinia virus strain LC16m8 so as to induce homologous recombination in the hemagglutinin (HA) gene region of the vaccinia virus, thereby preparing recombinant vaccinia viruses (rVV-CN5, rVV-CN2 and rVV-N25) expressing the respective proteins of HCV.

Here, the vaccinia virus strain LC16m8 that is used for preparing the recombinant vaccinia virus can be proliferated in an individual animal, but it is an attenuated strain whose proliferating property is extremely low in nerve cells. This strain is approved as a smallpox vaccine in Japan, where no serious side effect has been caused upon vaccination for about 50,000 children (research report from the Smallpox Research Group, Ministry of Health and Welfare, Clinical Virology, Vol. 3, No. 3, 269, 1975). On the other hand, its immunity inducing capacity is reported to be comparable to that of the parent Lister strain, and thus strain LC16m8 is a safe and effective vaccine.

Since HCV protein gene is inserted into the HA gene region of the vaccinia virus in the prepared rVV-CN5, rVV-CN2 and rVV-N25, HA protein expression is deleted and thus no hemagglutination is observed. Accordingly, hemagglutination of avian erythrocyte with plaques formed by infecting animal cells with rVV-CN5, rVV-CN2 and rVV-N25 is used as an indicator for screening the recombinant vaccinia virus. The recombinant vaccinia virus of interest can be obtained by selecting a white plaque with no hemagglutinin.

The virus obtained from the white plaque may be subjected to PCR using virus genome as a template and HCV gene-specific primers to confirm gene transfer of HCV.

Expression of HCV protein can be confirmed by Western blotting method using animal cells infected with rVV-CN5, rVV-CN2 and rVV-N25 as samples. Here, as the antibody, IgG purified from an antiserum prepared by HCV polypeptide immunization (J. Biol. Chem. 279:14531-14541, 2004) using Protein G can be used.

If not the HA gene region, the thymidine kinase (TK) gene region is usually used as the insertion site for the gene of interest upon preparation of the recombinant vaccinia virus. If the gene of interest is inserted into the TK gene region, TK expression is deleted by which the proliferating property of the recombinant vaccinia virus is known to be reduced. Meanwhile, it is reported that deletion of HA protein expression have little effect on the proliferating property of the recombinant vaccinia virus (Vaccine 12, 675-681, 1994). Hence, according to the present invention, the HA gene region is preferable as the insertion site for the gene of interest.

3. DNA Vaccine (Recombinant Vector)

Hereinafter, the (b) recombinant vector (so-called DNA vaccine) mentioned in Item 1 above and a method for preparing the same and else will be described.

A DNA vaccine is a gene-transporting vector (plasmid or virus) incorporating a desired gene (HCV genome-derived cDNA according to the present invention), which is administered to a patient or the like so that the cell incorporating this DNA vaccine generates a protein or a peptide expressed from said desired gene. The generated protein or the like stimulates the immune system and induces the antibody thereof. Since the DNA vaccine stays within the body for a long period of time after the administration and continues gradual generation of the protein or the like, excessive immune reaction can be avoided and its simple structure allows modification (Tang D C et al., Nature 356: 152-154, 1992; Barry M A et al., Nature 377: 632-635, 1995). Furthermore, it is advantageous in that the immune reaction induced in the host is type Th2 (Tang D C et al., Nature 356: 152-154, 1992; Ulmer J B et al., Science 259: 1745-1749, 1993; Hoffman S L et al., Ann N Y Acad Sci 772: 88-94, 1995).

The DNA vaccine used in the present invention may be a plasmid vector or a virus vector incorporating cDNA similar to the HCV genome-derived cDNA or the like (including variants of said cDNA) incorporated in the recombinant vaccinia virus described in Item 2 above or a corresponding RNA. Specifically, preferable examples of the DNA vaccine used in the present invention include, but not limited to, the above-mentioned plasmid vectors pBMSF7C-CN5, pBMSF7C-CN2 and pBMSF7C-N25.

4. Pharmaceutical Composition for Treating and/or Preventing Hepatitis C

The pharmaceutical composition of the present invention is a pharmaceutical composition comprising a combination of the (a) recombinant vaccinia virus and the (b) recombinant vector described in Item 1 above, or a pharmaceutical composition comprising a combination of the (c) recombinant vaccinia virus and the (d) recombinant vaccinia virus.

For the above-described combinational use, it is important that the nucleotide sequence of all or a part of cDNA of HCV genome contained (incorporated) in the (a) recombinant vaccinia virus above is different from the nucleotide sequence of all or a part of cDNA of HCV genome contained (incorporated) in the (b) recombinant vector above.

Similarly, for the above-described combinational use, it is important that the nucleotide sequence of all or a part of cDNA of HCV genome contained (incorporated) in the (c) recombinant vaccinia virus above is different from the nucleotide sequence of all or a part of cDNA of HCV genome contained (incorporated) in the (d) recombinant vaccinia virus above.

Since the incorporated cDNAs of HCV genome have different nucleotide sequences from each other as described above, they can exert a remarkable effect as described above, namely an effect of very strong specific cell-mediated immune induction.

The combination of the HCV genome-derived cDNAs incorporated into the (a) recombinant vaccinia virus above and the (b) recombinant vector above, and the combination of the HCV genome-derived cDNAs incorporated into the (c) recombinant vaccinia virus above and the (d) recombinant vaccinia virus above are not particularly limited, and can arbitrarily be selected from the various HCV genome-derived cDNAs described in Item 2 above that can be used in the present invention. Examples of the combination include, but not limited to, a combination where N25 is incorporated into the (a) recombinant vaccinia virus above while CN2 is incorporated into the (b) recombinant vector above, or vice versa, and combination where N25 is incorporated into the (c) recombinant vaccinia virus while CN2 is incorporated into the (d) recombinant vaccinia virus above, or vice versa.

Moreover, in a pharmaceutical composition of the present invention, when the combination of the (a) recombinant vaccinia virus above and the (b) recombinant vector above is employed, it is important that either one of them is administered for a primary immunization and then the other for a boost immunization. Similarly, when the combination of the (c) recombinant vaccinia virus above and the (d) recombinant vaccinia virus above is employed, it is important that either one of them is administered for a primary immunization and then the other for a boost immunization. According to the present invention, the administration for the primary immunization may be performed in multiple doses (preferably twice) and the administration for the boost immunization may be performed in multiple doses (preferably twice). For example, a preferable dosing schedule may include administrations for the primary immunization twice on Week 0 and Week 2 followed by an administration for the boost immunization on Week 4, or an administration for the primary immunization on Week 0 followed by administrations for the boost immunization twice on Week 2 and Week 4. The method for inducing cell-mediated immunity in which different types of vaccines are sequentially administered in two stages, i.e., the primary immunization and the boost immunization, is characteristic of the prime-boost method.

The present invention can also provide a method for treating and/or preventing hepatitis C, comprising: administering either one of a (a) recombinant vaccinia virus below or a (b) recombinant vector below to a test animal (patient) for a primary immunization; and then administering the other for a boost immunization:

(a) a recombinant vaccinia virus comprising an expression promoter, and all or a part of cDNA of hepatitis C virus genome; and (b) a recombinant vector comprising an expression promoter, and all or a part of cDNA of hepatitis C virus genome (provided that it has a nucleotide sequence that differs from that of all or a part of cDNA of hepatitis C virus genome contained in the (a) recombinant vaccinia virus).

In addition, the present invention can also provide use of a pharmaceutical composition of the present invention for treating and/or preventing hepatitis C, specifically, use of the (a) recombinant vaccinia virus above and the (b) recombinant vector above, in particular, use of either one of the (a) recombinant vaccinia virus above or the (b) recombinant vector above for a primary immunization and the other for a boost immunization.

The present invention can further provide a method for treating and/or preventing hepatitis C, comprising: administering either one of a (c) recombinant vaccinia virus below or a (d) recombinant vaccinia virus below to a test animal (patient) for a primary immunization; and then administering the other for a boost immunization:

(c) a recombinant vaccinia virus comprising an expression promoter, and all or a part of cDNA of hepatitis C virus genome; and (d) a recombinant vaccinia virus comprising an expression promoter, and all or a part of cDNA of hepatitis C virus genome (provided that it has a nucleotide sequence that differs from that of all or a part of cDNA of hepatitis C virus genome contained in the (c) recombinant vaccinia virus).

In addition, the present invention can also provide use of a pharmaceutical composition of the present invention for treating and/or preventing hepatitis C, specifically, use of the (c) recombinant vaccinia virus above and the (d) recombinant vaccinia virus above, in particular, use of either one of the (c) recombinant vaccinia virus above or the (d) recombinant vaccinia virus above for a primary immunization and the other for a boost immunization.

A pharmaceutical composition of the present invention may be introduced into an organism by any known method, for example, but not limited to, by intramuscular, intraperitoneal, intradermal or subcutaneous injection; nasal, buccal or lung inhalation; or oral administration. Additionally, the recombinant vaccinia virus contained in the pharmaceutical composition of the present invention may be administered in combination with an existing antiviral drug (e.g., interferon). An embodiment of these combinational administrations is not particularly limited. The recombinant virus of the present invention can be administered simultaneously with the existing antiviral drug, or they may be introduced into an organism according to a method in which one is administered after the other after a certain period of time.

Furthermore, a pharmaceutical composition of the present invention may also be mixed with a known pharmaceutically acceptable carrier such as an excipient, a bulking agent, a binder or a lubricant, a buffer, a tonicity agent, a chelating agent, a colorant, a preservative, a fragrance, a flavoring agent, a sweetener or the like.

A pharmaceutical composition of the present invention may orally or parenterally be administered according to its form including oral agents such as a tablet, a capsule, a powdered agent, a granular agent, a pill, a solution, syrup or the like, or parenteral agents such as an injection, a topical agent, a suppository or an eye drop. Preferable examples include local injections such as intradermal, intramuscular and intraperitoneal injections.

Although a dosage may appropriately be chosen according to the type of the active element, the administration route, the subject of administration, age, weight, sex and symptoms of the patient, and other conditions, the daily dosage of the recombinant vaccinia virus (vaccinia vaccine) or the recombinant vector (DNA vaccine) is about 1,000-1,000,000,000 PFU (plaque forming units) and preferably about 100,000-100,000,000 PFU in the case of oral administration, while it is about 100-1,000,000,000 PFU and preferably about 1000-100,000,000 PFU in the case of parenteral administration. The recombinant vaccinia virus (vaccinia vaccine) or the recombinant vector (DNA vaccine) may be administered once or several times a day.

It is preferable that the antibody titer or the cell-mediated immunity activity as a vaccine is measured beforehand for the recombinant vaccinia virus (vaccinia vaccine) or the recombinant vector (DNA vaccine) used in the present invention.

For example, the antibody titer against rVV-CN5, rVV-CN2, rVV-N25 or parent strain LC16m8 as the recombinant vaccinia virus (vaccinia vaccine) can be determined by inoculating rabbits with these virus strains and sequentially collecting the sera so as to measure the ELISA values against HCV in the sera. The antibody titer of the recombinant vector (DNA vaccine) can also be measured in the same manner as described above.

Moreover, the cell-mediated immunity activity can be measured by inoculating mice with rVV-CN5, rVV-CN2, rVV-N25 or parent strain LC16m8 and then isolating the spleen cells from the immunized mice so as to determine whether or not HCV-specific CTL (cytotoxic T cell) is induced by ELISPOT assay. The cell-mediated immunity activity of the recombinant vector (DNA vaccine) can also be measured in the same manner as described above.

Hereinafter, the present invention will be described more specifically by way of examples, although the present invention should not be limited thereto.

Example 1

Transgenic Mouse

Transgenic (HCV-Tg) mice (CN2-29$^{(+/-)}$/MxCre$^{(+/-)}$ (MxCre/HCR6-CN2), RzCN5-15$^{(+/-)}$/MxCre$^{(+/-)}$ (MxCre/HCR6-RzB15)) in which expression of HCV gene can be induced at any time by administering poly(I:C) (FIG. 1B), and C56BL/6 mice were used.

The HCV-Tg mice that were administered with poly(I:C) to allow continuous expression of HCV protein for 3 months were used for experiments. The CN2-29$^{(+/-)}$/MxCre$^{(+/-)}$ mice coded for a part of HCV gene while the RzCN5-15$^{(+/-)}$/MxCre$^{(+/-)}$ mice coded for full-length HCV gene.

Example 2

Preparation of HCV Gene Expression Vaccine (DNA Vaccine)

HCV-DNA vaccines (HCV-CN2 (or CN2 DNA) and HCV-N25 (or N25 DNA)) prepared from pBMSF7C plasmid vector containing all regions of the HCV gene (FIG. 1A) by inserting gene regions substantially coding for structural protein regions (CN2) of HCV and gene regions substantially coding for non-structural protein regions (N25) of HCV into pCAGGS plasmid vectors, respectively by PCR method and restriction enzyme reaction were used as a primary vaccine (vaccine for a primary immunization) or a booster vaccine (vaccine for a boost immunization) (FIG. 1C). A DNA vaccine without the HCV gene regions (emp) was used as a control for these vaccines. In addition, rVV-CN2 and rVV-N25, namely, recombinant vaccinia viruses (rVV) obtained by inserting the same sequences as the sequences incorporated in the DNA vaccines into vaccinia virus strains LC16m8, were used as either the primary vaccine or the booster vaccine (FIG. 1C).

Example 3

Preparation of Recombinant Vaccinia Viruses (Vaccinia Vaccines)

All gene regions of hepatitis C virus (CN5) and gene regions coding for the structural protein regions building the capsid (CN2) and the gene regions cording for the non-structural protein regions involved in replication (N25) (DDBJ/EMBL/GenBank accession number; AY045702) were each inserted into SbfI and SgfI sites of pBMSF7C plasmid (see Japanese Unexamined Patent Application Publication No. Heisei 6-237773) to prepare plasmid vectors pBMSF7C-CN5, pBMSF7C-CN2 and pBMSF7C-N25, in which HCV genome-derived genes were inserted downstream of the ATI/p7.5 hybrid promoter within the hemagglutinin (HA) gene region.

Primary rabbit kidney culture cells were seeded in a T175 flask. Once the cells reached confluence, the attenuated vaccinia virus strain LC16m8 was used for infection at moi=10 and 30° C. for two hours. The term moi (multiplicity of infection) refers to PFU per cell. After the infection, the virus solution was removed by suction and the cells were washed with PBS(−). Subsequently, the cells were subjected to a treatment with 0.05% trypsin/0.5 mM EDTA/PBS(−), washed with a 10% FCS/MEM medium, PBS(−) and a HeBS buffer, and then the cells were suspended in 600 µl of a HeBS buffer. 40 µg each of the plasmid vectors pBMSF7C-CN5, pBMSF7C-CN2 and pBMSF7C-N25 was diluted in a HeBS buffer to a total amount of 200 µl, which was added to and mixed with the cell suspension and left to stand still on ice for 10 minutes. The cell suspension added with the plasmid vector was transferred into a 0.4 cm cuvette and subjected to electroporation (0.2 kV, 960 µF) using an electroporator (Bio-Rad). Immediately after the electroporation, 1 ml of a 10% FCS/MEM medium was added to the cell suspension for dilution. This cell suspension was added to RK13 cells or primary rabbit kidney culture cells that had been seeded in a T175 flask in advance and cultured at 30° C. for 24 hours.

After 24 hours of culture, the culture supernatant was removed by suction and the cells were washed with PBS(−). Subsequently, the cells were subjected to a treatment with 0.05% trypsin/0.5 mM EDTA/PBS(−), and then suspended in a 10% FCS/MEM medium. The cell suspension was collected, subjected to ultrasonic treatment (30 sec×4 times) in cold water, and then centrifuged (2000 rpm, 10 min). The resulting supernatant was used as the virus solution. The virus solution was diluted in a 10% FCS/MEM medium, and used to infect primary kidney culture cells that had been seeded in a 100 mm dish at 30° C. for an hour. After removing the virus solution by suction, the cells were washed with PBS(−). A 10% FCS/0.5% methyl cellulose/ MEM medium was added to culture at 30° C. for 72 hours. 72 hours later, the supernatant was removed by suction and the resultant was washed with PBS(−). A PBS(+)-diluted avian erythrocyte solution was added to the 100 mm dish to culture at 37° C. for 30 minutes. The erythrocyte solution was removed by suction and the cells were washed with PBS(−) twice. Plaques that did not adsorb the avian erythrocytes were collected using a Pipetman. The collected plaques were subjected to PCR and gene sequencing to confirm transfer of HCV gene. The plaques confirmed with gene transfer were subjected to repeated plaque purification for three times.

Viruses isolated after three times of plaque purification were subjected to small-scale culture. The colony obtained after the third purification was suspended in 700 µl of 10% FCS/MEM medium and subjected to an ultrasonic treatment in cold water. After centrifugation (2000 rpm, 10 min), 500 µl of the supernatant was added to primary kidney culture cells that had been seeded in a T25 flask for infection at 30° C. for 2 hours. After the infection, the virus solution was removed by suction and the cells were washed with 2.5 ml of 10% FCS/MEM medium. The medium was removed by suction and 2.5 ml of 10% FCS/MEM medium was freshly added to culture at 30° C. for 72 hours. 72 hours later, the cells were scraped off from the flask using a scraper and the cell suspension was collected. The collected cell suspension was subjected to an ultrasonic treatment (30 sec, 4 times) in cold water followed by centrifugation. The resulting supernatant was collected as a virus solution. The collected virus solution was serially diluted and added to RK13 cells or primary rabbit kidney culture cells that had been seeded in a 6-well plate for infection at 30° C. for an hour. The virus solution was removed by suction, the cells were washed twice with PBS(−), and then a 10% FCS/0.5% methyl cellulose/MEM medium was added to culture at 30° C. for 72 hours. 72 hours later, the number of plaques formed in the well was counted to determine the titer.

A large-scale culture was conducted based on the determined titer. RK13 cells or primary rabbit kidney culture cells were seeded in ten T175 flasks. Once the cells reached confluence, the recombinant vaccinia virus solution was used for infection at moi=0.1 and 30° C. for two hours. After the infection, the virus solution was removed by suction and the cells were washed with 20 ml of 10% FCS/MEM medium. The medium was removed by suction and 20 ml of 10% FCS/MEM medium was freshly added to culture at 30° C. for 72 hours. 72 hours later, the cells were scraped off from the flask using a scraper and the cell suspension was collected, frozen and stored at −80° C. After three freeze-thaw cycles of this cell suspension, the resultant was subjected to ultrasonic treatment (30 sec, 4 times) in cold water and centrifuged. The resulting supernatant was collected as a virus solution. The collected virus solution was transferred into a high-speed centrifugal tube and centrifuged at 18,000 rpm for 45 minutes to precipitate the virus. The supernatant was removed by suction and thereafter the pellets were resuspended in a small amount of 10% FCS/MEM medium. By this procedure, a virus solution having a concentration 10-times higher than that obtained upon the culture in the T175 flask can be prepared. This concentrated virus solution was serially diluted and used to infect RK13 cells or primary kidney culture cells that had been seeded in a 6-well plate to determine the virus titer in the solution by a method similar to the above-described method. This concentrated virus solution having the determined titer was used in various experiments in the following examples.

Example 4

Immunization Method

100 µg of DNA vaccine suspended in 25 µl of PBS was administered twice in a two-week interval to the muscles of the mouse lower legs by electroporation (50 V, 99 msec, 8 times). The recombinant vaccinia virus was intradermally administered at the back at $1 \times 10^8$ pfu/50 µl. Two weeks after the last administration, the spleens and the livers were collected for analysis.

Example 5

Determination of Specific Cell-Mediated Immune Inducing Capacity by ELISPOT Method Spleen cells ($1 \times 10^5$) that were subjected to an erythrocyte hemolysis treatment or $CD8^+$ and $CD4^+$ cells ($2 \times 10$) obtained by separating the spleen cells using magnetic beads (Miltenyi Biotec) were stimulated with stimulating cells that had been pretreated with mitomycin (tumor cells in which each HCV gene site was overexpressed (EL-4/CN2, /C, /E2, /NS2, /N3-4A)) ($1 \times 10^4$) and cultured at 37° C. for 48 hours in a 5% $CO_2$ incubator to determine the HCV-antigen-specific IFN-γ-producing cells by an ELISPOT method.

(Day 1)

A purified anti-mouse IFN-γ antibody (R4-6A2) (1 mg/ml) (Pharmingen) was adjusted to have a final concentration of 8 µg/ml (125-fold diluted in sterile PBS), seeded at 75-100 µl/well in a 96-well nitrocellulose plate and left to stand still at 4° C. overnight.

(Day 2)

Spleen cells were taken from the mouse and a moderate amount of them were allowed to be suspended in washing RPMI. As the washing RPMI, RPMI supplemented with 2.5% FCS was used. The resultant was centrifuged at 1,200 rpm and 4° C. for 5 minutes to collect the cells. The cells were treated with ACK (ammonium chloride potassium), allowed to be suspended in washing RPMI, and centrifuged again at 1,200 rpm and 4° C. for 5 minutes to collect the cells. 500 µl of washing RPMI and then the suspended cell were passed through a filter. After the solution was completely passed through the filter, the resultant was washed with 1.5 ml of washing RPMI. The cells were washed once with 10% FCS-supplemented RPMI and allowed to be suspended in a H-h medium at 1×10⁷/ml.

1) H-h medium: A mixture of equal amounts of 10% FCS-supplemented RPMI and 10% FCS-supplemented CLICK'S medium 2) 10% FCS-supplemented RPMI: RPMI-1640 (SIGMA R8758), FCS (final 10%), 2-mercaptoethanol (final concentration 5 μM), penicillin-streptomycin (final concentrations PCs: 100 μ/ml, SM:0.1 mg/ml), 7.5% NaHCO₃ 4 ml 3) 10% FCS-supplemented CLICK'S medium: CLICK'S medium (SIGMA C5572), FCS (final concentration 10%), 2-mercaptoethanol (final concentration 5 μM), penicillin-streptomycin (final concentrations PCs: 100 μ/ml, SM:0.1 mg/ml), 7.5% NaHCO₃ 4 ml Initiating Culture The above-described 96-well nitrocellulose plate was washed with PBS (100 μl/well) for three times, then added with 10% FCS-supplemented RPMI at 100 μl/well, and subjected to blocking at 37° C. for an hour in a $CO_2$ incubator. The medium was discarded and effector cells were seeded in 2-fold serial dilutions from 1×10⁶/100 μp/well to 0.125×10⁶/100 μl/well.

A peptide solution (200 μg/ml) was added at 100 μl/well (final concentration 100 μg/ml) and cultured at 37° C. for 24 hours in a $CO_2$ incubator.

(Day 3)

The medium was discarded and the resultant was washed with PBS, 0.05% Tween (200 μl/well) for ten times. Biotinylated anti-mouse IFN-γ (XMG1.2) (0.5 mg/ml) (Pharmingen) was adjusted to have a final concentration of 2 μg/ml (250-fold diluted in PBS) and added at 100 μl/well. The resultant was left to stand at 4° C. overnight.

(Day 4)

The above-described 96-well nitrocellulose plate was washed with PBS, 0.05% Tween 20 (200 ul/well) for ten times. Streptavidin-alkaline phosphatase (1 mg/ml) (MABTECH AB) was adjusted to have a final concentration of 1 μg/ml (1000-fold diluted in PBS) and added at 100 μl/well.

The resulting solution was left to stand at room temperature for 1.5 hours. A 25× AP color development buffer (BIO-RAD) was 25-fold diluted in DW, 1/100 volume each of AP color reagents A and B (BIO-RAD) were added to prepare a reaction mixture. The above-described 96-well nitrocellulose plate was washed with PBS, 0.05% Tween 20 (200 μl/well) for ten times. The reaction mixture was added at 100 μl/well and left to stand at room temperature for 10-20 minutes. Once color was developed and a dark spot emerged, the reaction mixture was discarded and the resultant was thoroughly washed with water. The bottom of the 96-well nitrocellulose plate was scraped off and dried to count the number of spots with ELISPOT Reader.

Figure 2:
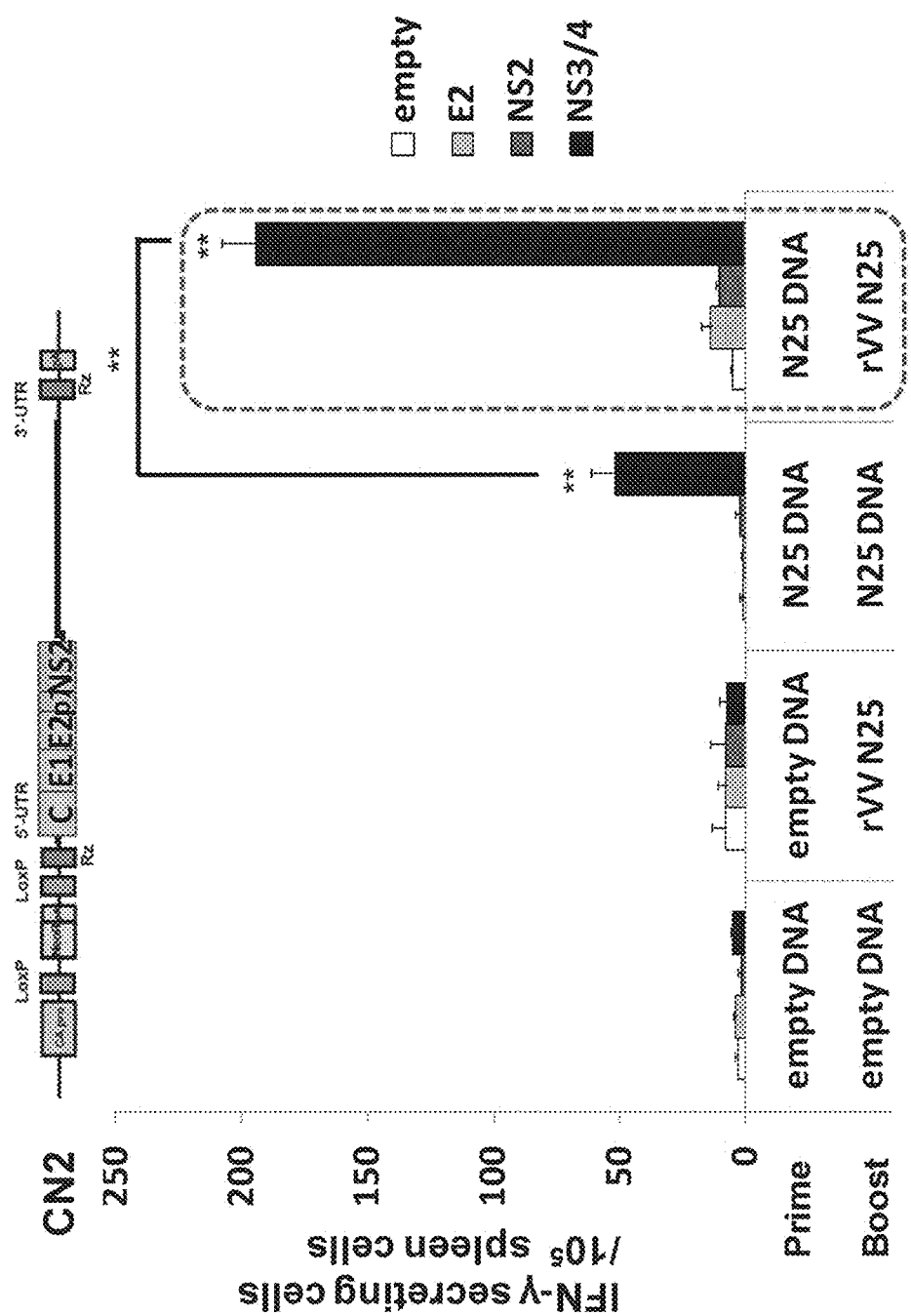
FIG. 2 is a diagram of results showing that a prime-boost vaccine comprising a combination of a HCV-DNA vaccine and rVV induced HCV-specific cell-mediated immunity reaction in partial-length HCV-coding Tg mice.

Spleens were removed from the C57BL/6 mice that had been administered with HCV-N25 vaccine and rVV-N25 to determine the HCV-antigen-specific IFN-γ-producing cell in the spleen cells by ELISPOT method. The spleen cells from the control group did not show any specific spot after the stimulation whereas significant production of IFN-γ was confirmed in the spleen cells from the HCV-N25-administered group after the stimulation with EL-4/E2, /NS2 and/N3-4A cells (FIG. 2). Similarly, production of IFN-γ was confirmed in the prime-boost group against EL-4/E2, /NS2 and/N3-4A cells.

Figure 3:
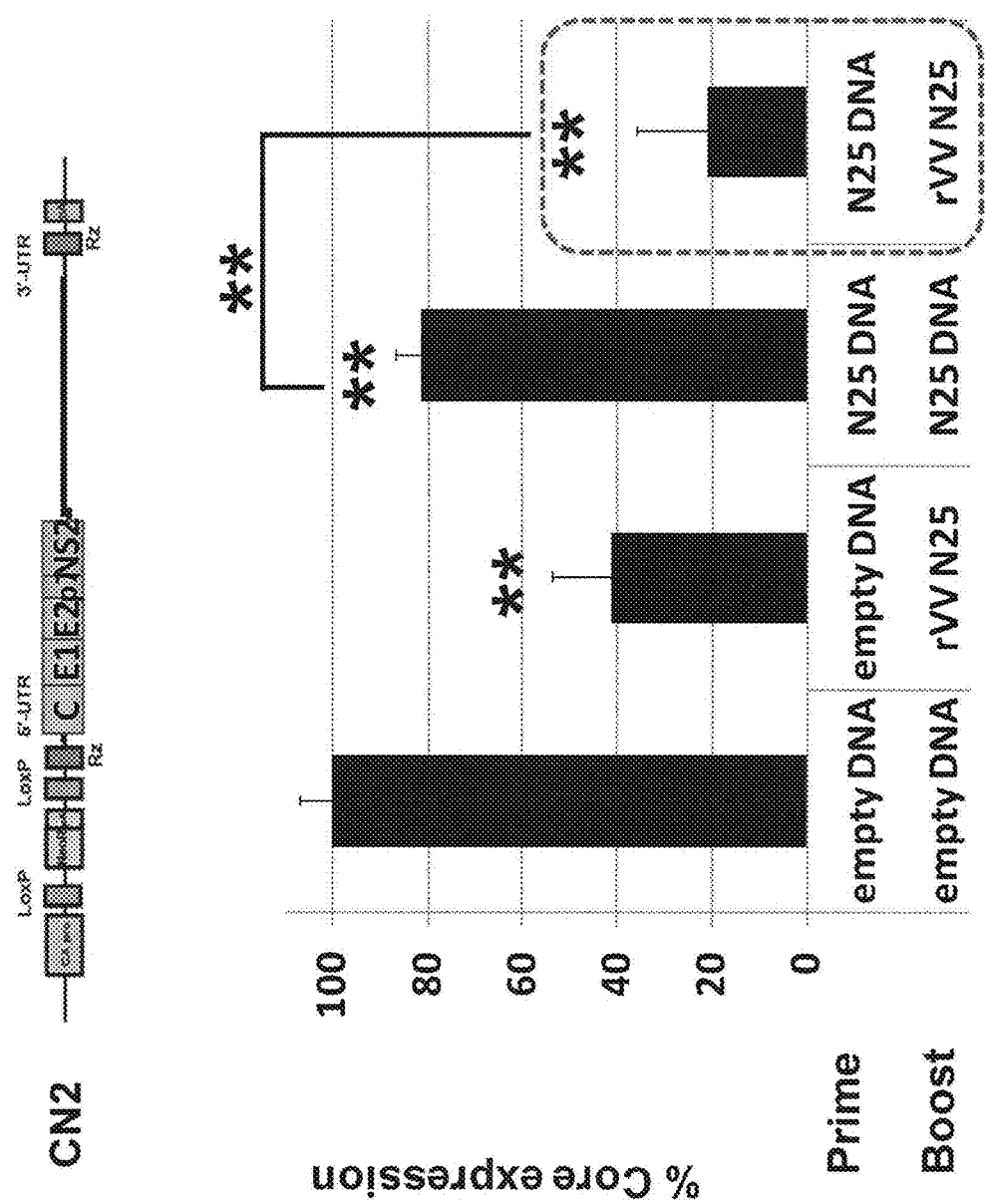
FIG. 3 is a diagram of results showing that a prime-boost vaccine comprising a combination of a HCV-DNA vaccine and rVV reduced the expression level of the core protein in liver to a more extent than a DNA vaccine alone.
Figure 4:
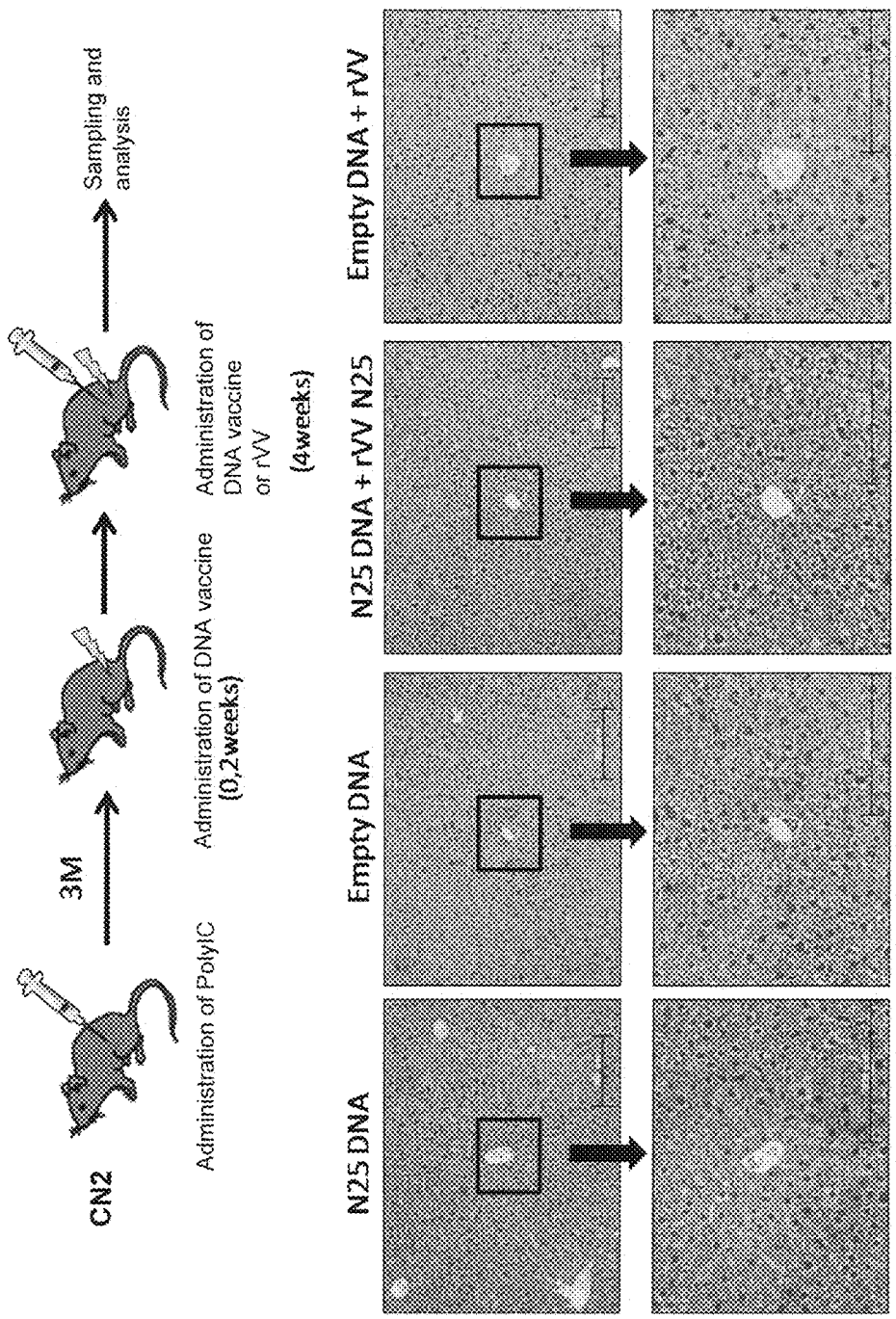
FIG. 4 is a picture showing results from morphological examination of livers after a prime-boost vaccine administration in partial-length HCV-coding Tg mice.
Figure 5:
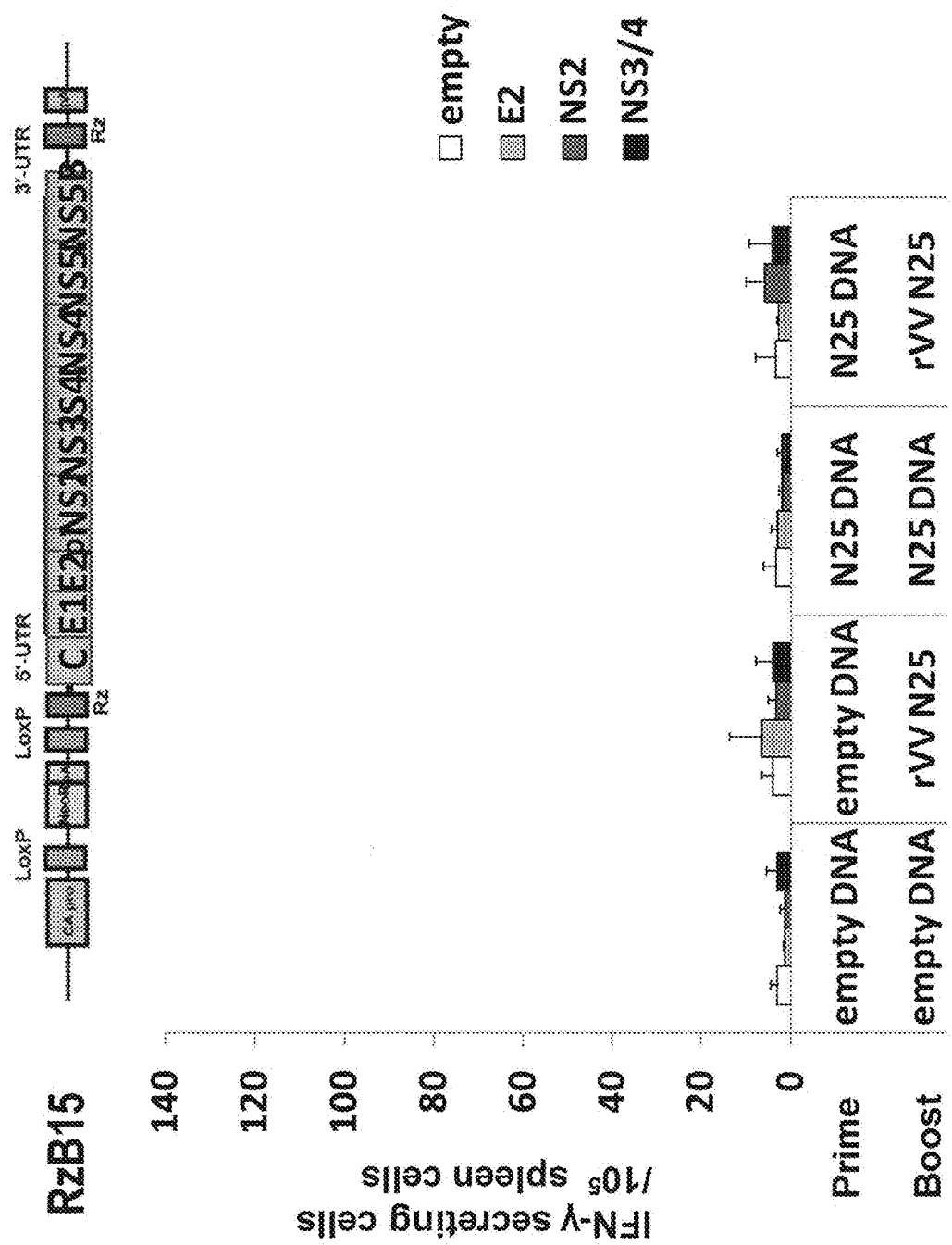
FIG. 5 is a diagram of results showing that activation of specific cell-mediated immunity was weak even with a prime-boost vaccine in full-length HCV-coding Tg mice.
Figure 6:
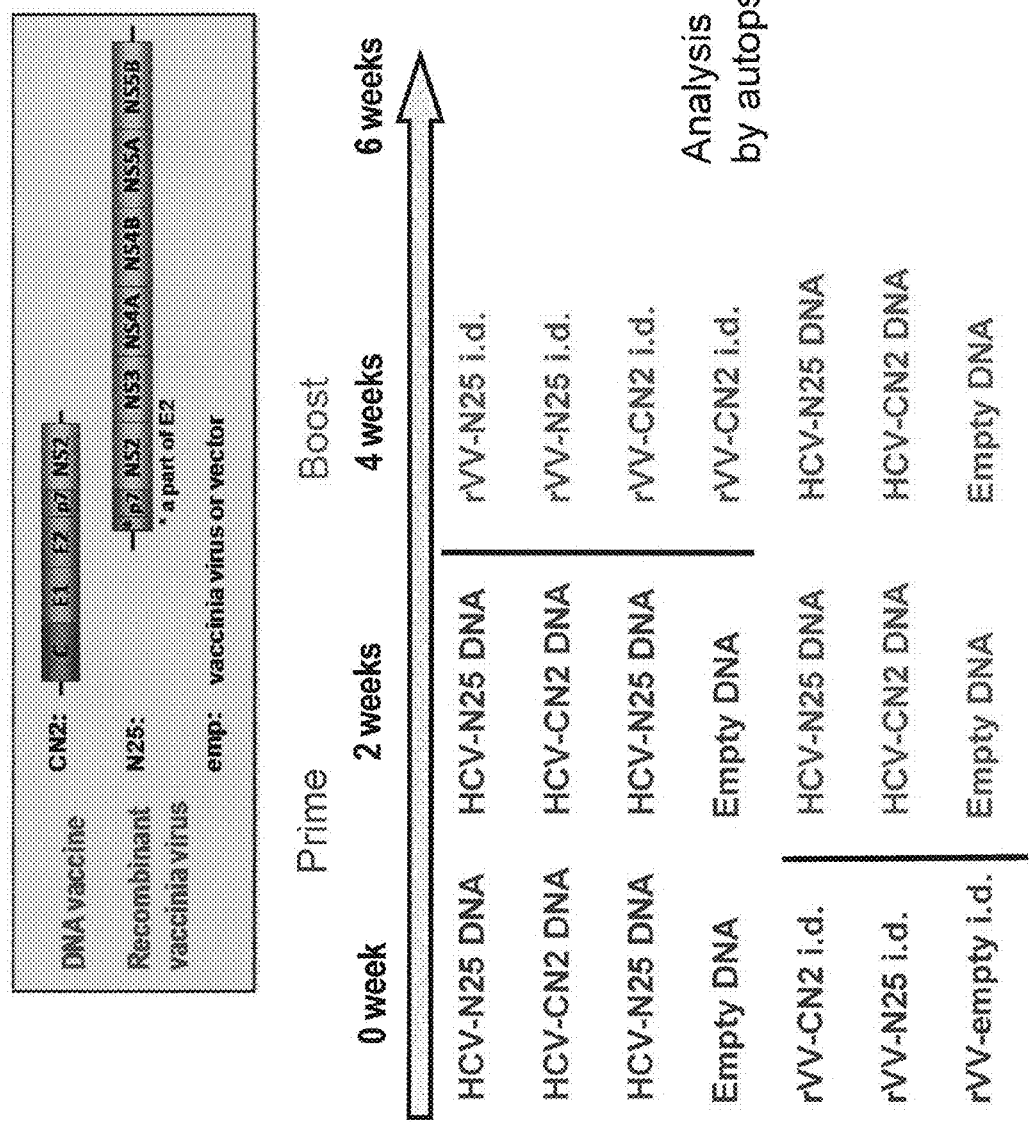
FIG. 6 is a diagram showing a process for developing a novel prime-boost vaccination.

The counted results are shown. FIG. 2 shows results of prime-boost vaccine inoculation with HCV-N25 and rVV-N25 in partial-length HCV Tg mice. In comparison to inoculation with HCV-N25 alone, the HCV-specific cell-mediated immunity reaction was induced stronger. FIG. 3 shows the amount of HCV core protein in the liver at that point, where elimination was stronger with the prime-boost vaccine inoculation with HCV-N25 and rVV-N25. FIG. 4 shows the liver tissues observed at that point, where the hepatitis was most ameliorated with the prime-boost vaccine inoculation with HCV-N25 and rVV-N25. As can be appreciated from FIG. 5, however, induction of HCV-specific cell-mediated immunity reaction was insufficient with the prime-boost vaccine inoculation with HCV-N25 and rVV-N25 in full-length HCV Tg mice. Accordingly, the combinations of the prime-boost vaccine inoculation were varied as shown in FIG. 6 for investigation.

Figure 7:
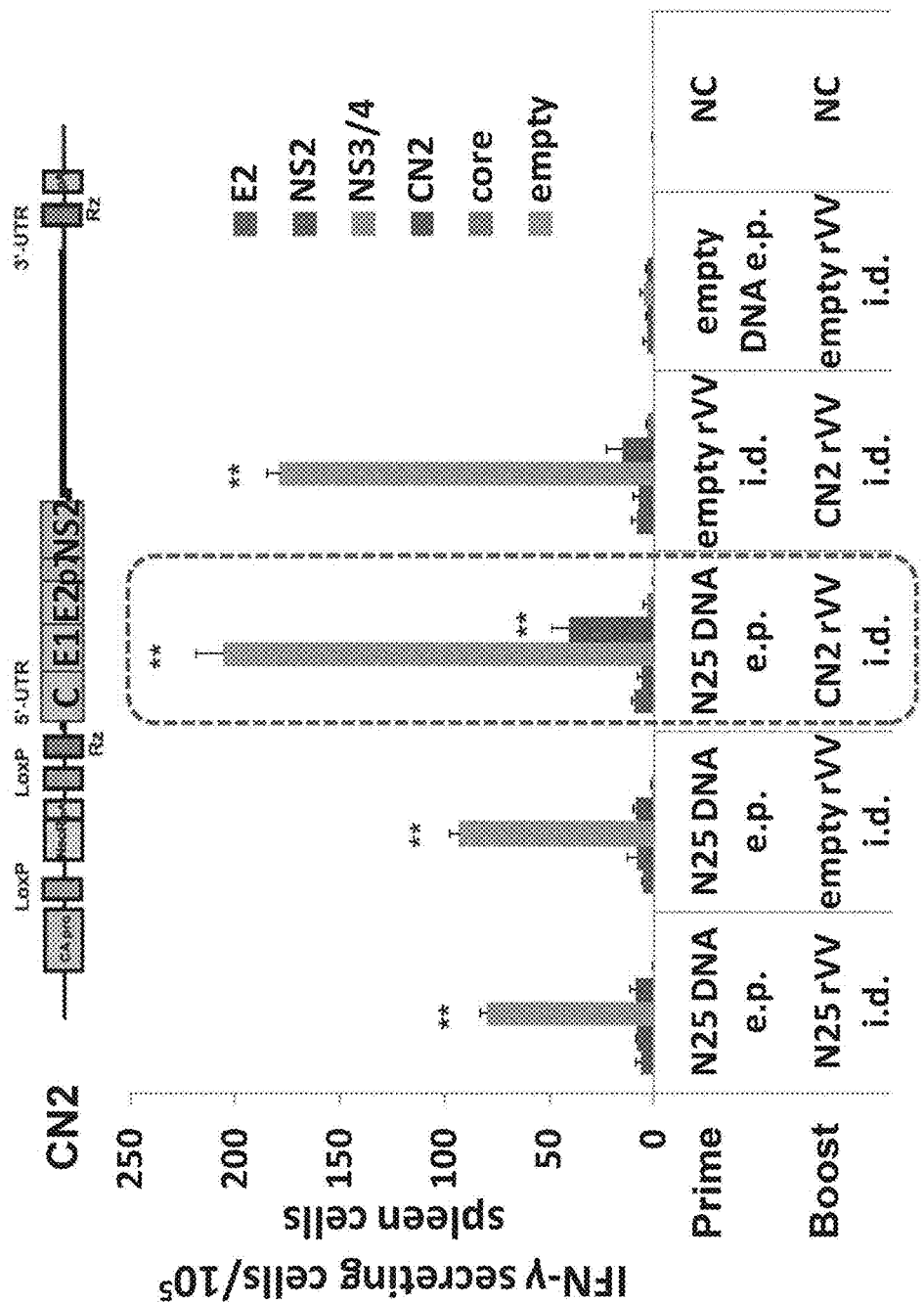
FIG. 7 is a diagram of results (part 1) showing that a combination of a DNA vaccine and a recombinant vaccinia virus (recombinant vaccinia vaccine) having different regions activated specific cell-mediated immunity to a more extent in partial-length HCV-coding Tg mice.
Figure 8:
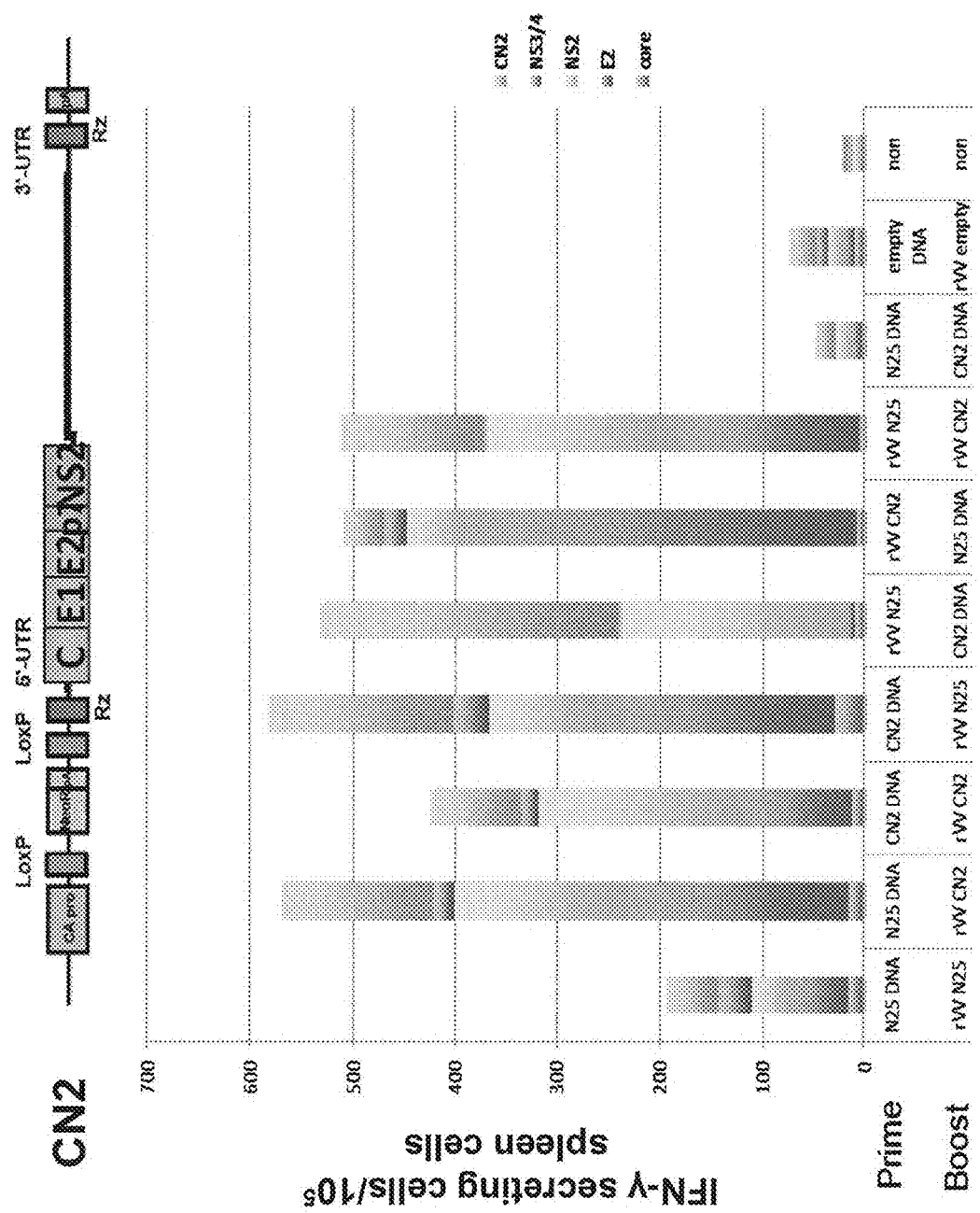
FIG. 8 is a diagram of results (part 2) showing that combinations of a DNA vaccine and a recombinant vaccinia virus (recombinant vaccinia vaccine) having different regions activated specific cell-mediated immunity to a more extent in partial-length HCV-coding Tg mice.
Figure 9:
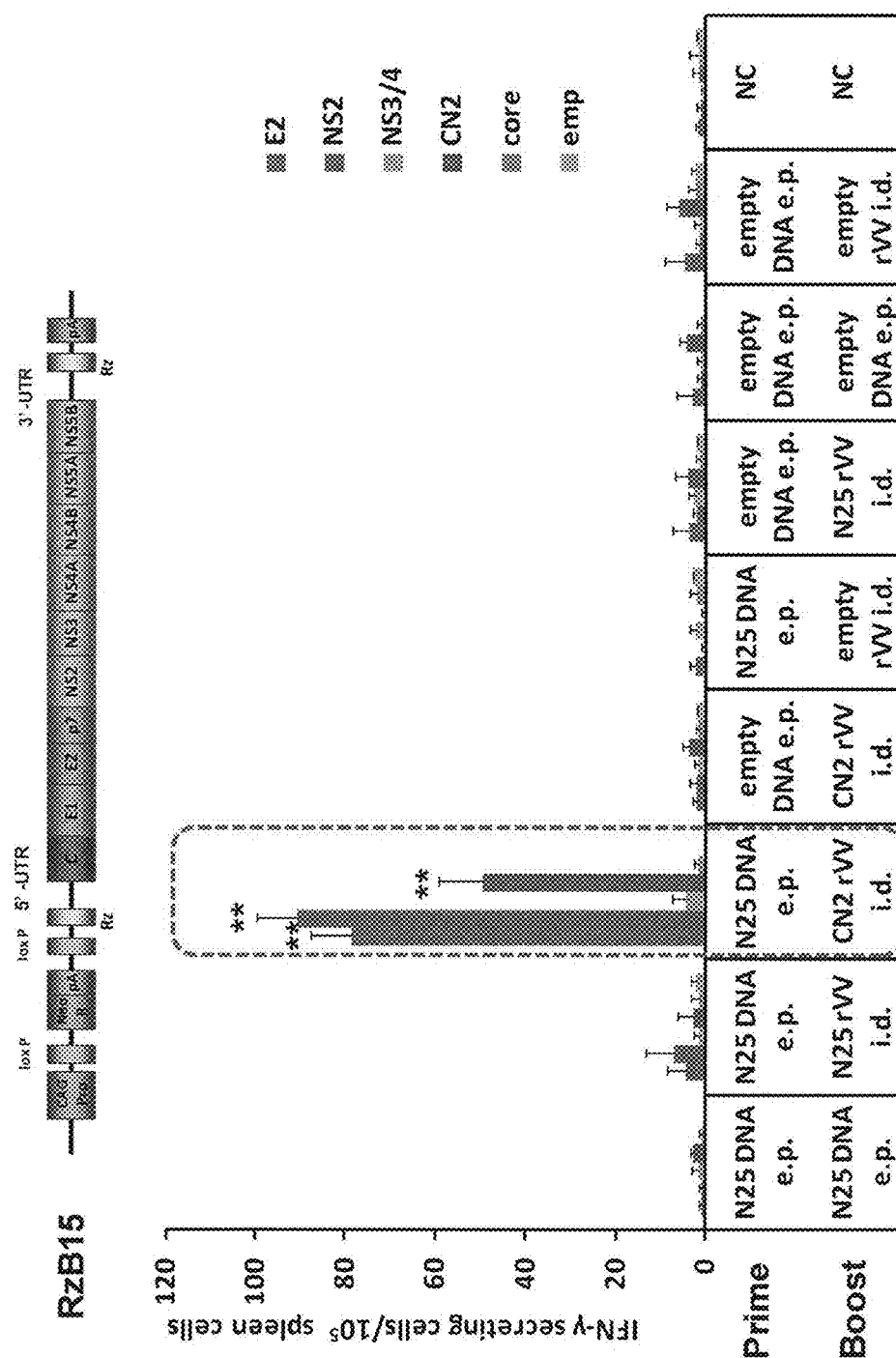
FIG. 9 is a diagram of results showing that a combination of a N25-DNA vaccine and CN2-rVV activated specific cell-mediated immunity even in strongly immunosuppressive full-length HCV-coding Tg mice.

As a result, combinations of different gene regions like the prime-boost vaccine inoculation with HCV-N25 and rVV-CN2 were found to strongly induce the HCV-specific cell-mediated immunity reaction as shown in FIG. 7. The results from analyses of other varied combinations are shown in FIG. 8. As long as different gene regions are combined as such, not only a prime-boost vaccine inoculation with HCV-DNA and rVV but also a prime-boost vaccine inoculation with rVVs having different gene regions was found to strongly induce the HCV-specific cell-mediated immunity reaction. When a prime-boost vaccine inoculation with HCV-N25 and rVV-CN2 as a combination of different gene regions was conducted in full-length HCV Tg mice, very strong induction of the HCV-specific cell-mediated immunity reaction was observed as shown in FIG. 9.

Example 6

Analysis of Liver

After vaccine administration, the livers were collected to prepare liver tissue extracts, which were subjected to formalin fixation. The expression levels of HCV core protein in the liver tissue extracts were quantified with commercially available HCV antigen ELISA kit (Ortho Clinical Diagnostics) (FIG. 3). The expression levels of HCV core protein in the livers decreased in all of the vaccine-administered groups as compared to the empty-administered group. In particular, the core protein expression level was confirmed to be most reduced in the prime-boost vaccine inoculated group (FIG. 3). The formalin-fixed liver sections were embedded in paraffin before preparing tissue sections, which were subjected to hematoxylin/eosin staining (FIG. 4). As a result of morphological examination of the livers, a number of morphological abnormalities such as swelling of the hepatic cells and irregular trabecular pattern were observed in the livers from the CN2-29$^{(+/-)}$/MxCre$^{(+/-)}$ mice that had been allowed to continuously express HCV protein for three months whereas these abnormalities were improved in the vaccine-administered group. In particular, remarkable improvement was confirmed in the prime-boost vaccine inoculated group (FIG. 4).

Figure 10:
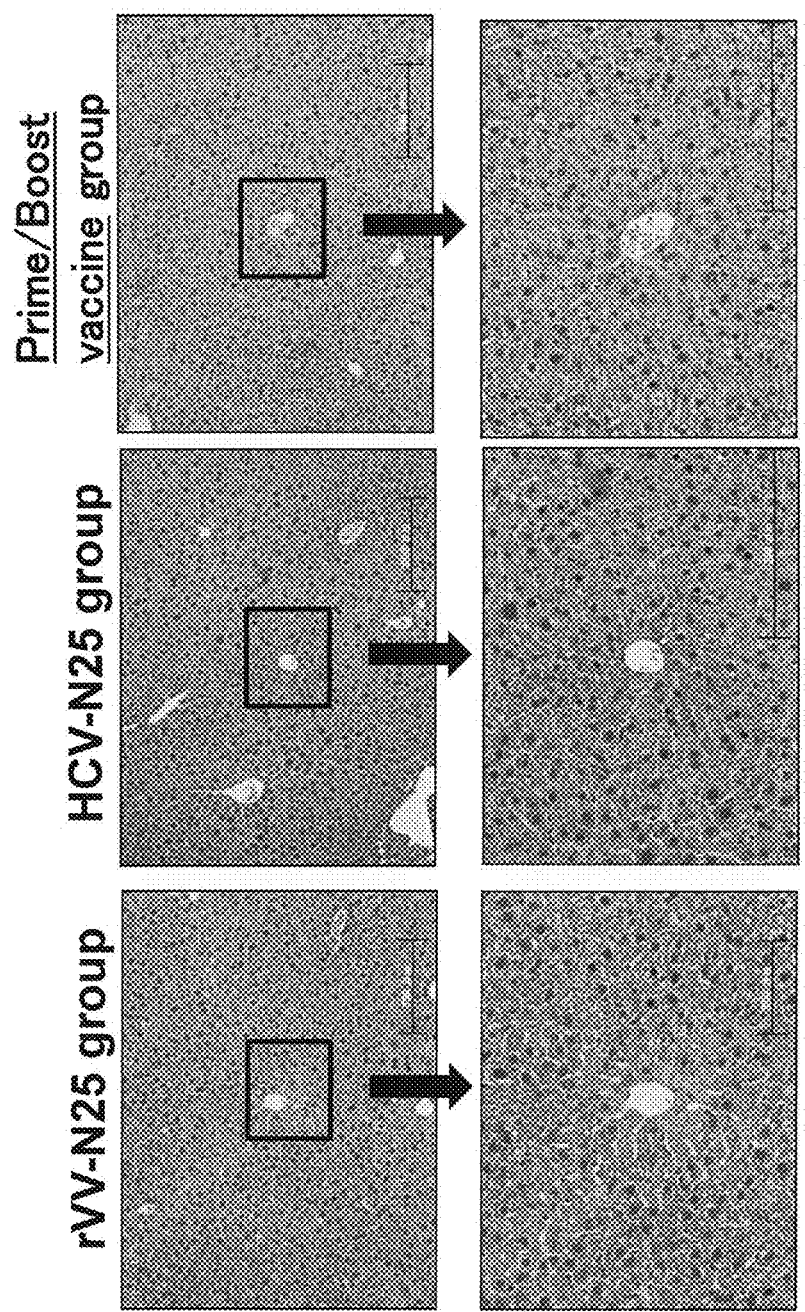
FIG. 10 is pictures showing results from morphological examination of mouse livers after a prime-boost vaccine administration in Rz15 full-length HCV-coding Tg mice. Referring to the pictures, the rVV-N25 group refers to those administered with N25 DNA (primary vaccine) and N25 rVV (booster vaccine), the HCV-N25 group refers to those administered with N25 DNA (primary vaccine) and N25 DNA (booster vaccine), and the prime-boost vaccine group refers to those administered with N25 DNA (primary vaccine) and CN2 rVV (booster vaccine).

Furthermore, a number of morphological abnormalities such as swelling of the hepatic cells and irregular trabecular pattern were also observed in the livers from the Rz15$^{(+/-)}$/MxCre$^{(+/-)}$ mice that had been allowed to continuously express HCV protein for three months whereas these abnormalities were improved in the vaccine-administered group. In particular, remarkable improvement was confirmed in the prime-boost vaccine inoculated group (FIG. 10).

INDUSTRIAL APPLICABILITY

The present invention can provide a pharmaceutical composition for treating and/or preventing hepatitis C that can further activate specific cell-mediated immunity and that is effective in completely eliminating HCV as compared to a case where a conventionally known vaccinia virus or DNA vaccine for hepatitis C is used alone.

The invention claimed is:

1. A pharmaceutical composition for treating and/or preventing hepatitis C, comprising a (a) recombinant vaccinia virus and a (b) recombinant vector below:
   (a) a recombinant vaccinia virus comprising an expression promoter and DNA of (i) or (ii) below:
   (i) DNA comprising the nucleotide sequence represented by SEQ ID NO:1; or
   (ii) DNA that comprises a nucleotide sequence having 90% or more identity to DNA comprising the nucleotide sequence represented by SEQ ID NO:1 and that codes for a structural protein and a non-structural protein of hepatitis C virus; and
   (b) a recombinant vector comprising an expression promoter and DNA of (iii) or (iv) below:
   (iii) DNA comprising the nucleotide sequence represented by SEQ ID NO:2; or
   (iv) DNA that comprises a nucleotide sequence having 90% or more identity to DNA comprising the nucleotide sequence represented by SEQ ID NO:2 and that codes for a structural protein and a non-structural protein of hepatitis C virus,
   wherein either one of the (a) recombinant vaccinia virus or the (b) recombinant vector is administered for a primary immunization, and then the other is administered for a boost immunization.

2. A pharmaceutical composition for treating and/or preventing hepatitis C, comprising a (a) recombinant vaccinia virus and a (b) recombinant vaccinia virus below:
   (a) a recombinant vaccinia virus comprising an expression promoter and DNA of (i) or (ii) below:
   (i) DNA comprising the nucleotide sequence represented by SEQ ID NO:1; or
   (ii) DNA that comprises a nucleotide sequence having 90% or more identity to DNA comprising the nucleotide sequence represented by SEQ ID NO:1 and that codes for a structural protein and a non-structural protein of hepatitis C virus; and
   (b) a recombinant vaccinia virus comprising an expression promoter and DNA of (iii) or (iv) below:
   (iii) DNA comprising the nucleotide sequence represented by SEQ ID NO:2; or
   (iv) DNA that comprises a nucleotide sequence having 90% or more identity to DNA comprising the nucleotide sequence represented by SEQ ID NO:2 and that codes for a structural protein and a non-structural protein of hepatitis C virus,
   wherein either one of the (a) recombinant vaccinia virus or the (b) recombinant vaccinia virus is administered for a primary immunization, and then the other is administered for a boost immunization.

3. The pharmaceutical composition according to claim 1, wherein the expression promoter is a hybrid promoter.

4. The pharmaceutical composition according to claim 3, wherein the nucleotide sequence of the hybrid promoter is DNA of the following (a) or (b):
   (a) DNA comprising the nucleotide sequence represented by SEQ ID NO:4; or
   (b) DNA that comprises a nucleotide sequence having 90% or more identity to DNA comprising the nucleotide sequence represented by SEQ ID NO:4 and that has promoter activity.

5. The pharmaceutical composition according to claim 1, wherein the vaccinia virus is strain LC16m8.

6. A method for treating and/or preventing hepatitis C, comprising administrating to a patient in need thereof the pharmaceutical composition according to claim 1, wherein either one of the (a) recombinant vaccinia virus or the (b) recombinant vector is administrated for a primary immunization, and then the other is adminiatrated for a boost immunization.

7. A pharmaceutical composition for treating and/or preventing hepatitis C, comprising a (a) recombinant vaccinia virus and a (b) recombinant vector below:
   (a) a recombinant vaccinia virus comprising an expression promoter and DNA of (i) or (ii) below:
   (i) DNA comprising the nucleotide sequence represented by SEQ ID NO:2; or
   (ii) DNA that comprises a nucleotide sequence having 90% or more identity to DNA comprising the nucleotide sequence represented by SEQ ID NO:2 and that codes for a structural protein and a non-structural protein of hepatitis C virus; and
   (b) a recombinant vector comprising an expression promoter and DNA of (iii) or (iv) below:
   (iii) DNA comprising the nucleotide sequence represented by SEQ ID NO:1; or
   (iv) DNA that comprises a nucleotide sequence having 90% or more identity to DNA comprising the nucleotide sequence represented by SEQ ID NO:1 and that codes for a structural protein and a non-structural protein of hepatitis C virus,
   wherein either one of the (a) recombinant vaccinia virus or the (b) recombinant vector is administered for a primary immunization, and then the other is administered for a boost immunization.

* * * * *

SEQUENCE LISTING

<160> NUMBER OF SEQ ID NOS: 4

<210> SEQ ID NO 1
<211> LENGTH: 3093
<212> TYPE: DNA
<213> ORGANISM: Hepatitis C virus

<400> SEQUENCE: 1

| | | | | | |
|---|---|---|---|---|---|
| cgtagaccgt | gcatcatgag | cacaaatcct | aaccccaaa | gaaaaaccaa | acgtaacacc | 60 |
| aaccgccgcc | cacaggacgt | caagttcccg | ggtggtggtc | agatcgttgg | tggagtttac | 120 |
| ctgttgccgc | gcaggggccc | caggttgggt | gtgcgcgcga | ctaggaagac | ttccgagcgg | 180 |
| tcacaacctc | gtggaaggcg | acaacctatc | cccaaggctc | gccagcccga | gggcagggcc | 240 |
| tgggctcagc | ccgggtaccc | ttggcccctc | tatggcaacg | agggcatggg | gtgggcagga | 300 |
| tggctcctgt | caccccgcgg | ctcccggcct | agttggggcc | ccacggaccc | ccggcgtagg | 360 |
| tcgcgtaatt | tgggtaaggt | catcgatacc | ctcacatgcg | gcttcgccga | cctcatgggg | 420 |
| tacattccgc | tcgtcggcgc | cccctaggg | ggcgttgcca | gggccctggc | acatggtgtc | 480 |
| cgggttgtgg | aggacggcgt | gaactatgca | acagggaatt | tgcccggttg | ctctttctct | 540 |
| atcttcctct | tggctctgct | gtcctgtttg | accatcccag | cttccgctta | tgaggtgcgc | 600 |
| aacgtatccg | ggatatacca | tgtcacgaac | gactgctcca | actcaagtat | tgtgtatgag | 660 |
| gcagcggaca | tgatcatgca | taccccccggg | tgcgtgccct | gcgttcggga | gggcaactcc | 720 |
| tcccgttgct | gggtggcact | tactcccacg | ctagcgccaa | ggaatgccag | cgtccccact | 780 |
| acggcaatac | gacgccatgt | cgatttgctc | gttggggcgg | ctgctttctg | ctccgctatg | 840 |
| tatgtgggag | atctctgcgg | atctgttttc | cttgtctccc | agctgttcac | cttctcgccc | 900 |
| cgccggcatg | agacaataca | ggactgcaat | tgctcaatct | atcccggcca | cgtgtcaggt | 960 |
| caccgcatgg | cttgggacat | gatgatgaac | tggtcgccta | caacgcccct | ggtggtgtcg | 1020 |
| cagttactcc | ggatcccaca | agctatcgtg | gacatggtgg | cggggctca | ctgggtgtc | 1080 |
| ctagcgggcc | ttgcctacta | ttccatggtg | gggaactggg | ctaaggtatt | gattgtgatg | 1140 |
| ctacttttg | ccggcgtcga | cggggagacc | cgtgtgacag | gggggcagat | agccagaaat | 1200 |
| gcctactcgc | tcacgaccct | cttttcatct | gggtcggctc | agaacatcca | gctcataaac | 1260 |
| accaacggta | gctggcacat | caacaggact | gccctgaact | gcaatgactc | cctcaacacc | 1320 |
| gggtttcttg | ccgcgctgtt | ctacgcgcac | aagttcaacg | cgtccggatg | tccagagcgc | 1380 |
| ttggccagct | gccgccccat | tgacaagttc | gatcagggt | ggggtcccat | cacttatgct | 1440 |
| gagcagggcg | gccaggacca | gaggccttat | tgctggcact | acgcacctaa | accatgtggt | 1500 |
| attgtatccg | cgtcgaaggt | gtgtggtcca | gtgtattgtt | tcacccccaag | cccagttgta | 1560 |
| gtggggacga | ccgatcggtt | cggtgtccct | acgtatagct | gggggggagaa | tgagacagac | 1620 |
| gtgctgctcc | ttaacaacac | gcggccgccg | caaggcaact | ggttcggctg | tacgtggatg | 1680 |
| aacggcactg | ggttcaccaa | gacatgcggg | ggcccccgt | gtaacatcgg | gggggcggc | 1740 |
| aataacaccct | tgacctgccc | tacggactgt | ttccggaagc | accccgcggc | cacttacaca | 1800 |
| aaatgtggtt | cgggaccttg | gctgacaccc | aggtgcttgg | tagactaccc | atacaggctc | 1860 |
| tggcactacc | cctgcactgc | caactttacc | atcttcaagg | ttaggatgta | tgtaggggc | 1920 |
| gtggagcaca | ggctcgatgc | tgcatgcaat | tggacccgag | ggaacgttg | caacttggag | 1980 |
| gatagggata | gattgagct | cagccgcta | ctgctgtcta | caacagagtg | gcaggtgctg | 2040 |
| ccctgttctt | tcaccaccct | accggctctg | tccactggtt | taattcatct | ccatcagaac | 2100 |

-continued

```
atcgtggacg tgcaatacct gtacggtata gggtcggcag ttgtttcctt tgcaatcaaa      2160
tgggactata tcgtgatact tttcctcctc ctggcggacg cgcgcgtctg tgcctgcttg      2220
tggatgatgc tgctgatagc ccaggccgag gccgccttag aaaacctggt ggtcctcaat      2280
gcggcgtccg tggccggagc gcatggcatt ctctccttcc ttgtgttctt ctgtgccgcc      2340
tggtacatca agggcaagct ggtccccggg gcagcatatg ctttctatgg agtatggccg      2400
ctgctcctgc ttctgctggc cttaccacca cgagcttacg ctatggagcg ggagatggct      2460
gcatcgtgcg gaggcgcggt gtttgtaggt ctggtactct tgacttt gtc accatactat      2520
aaagagttcc tcgccaggct catatggtgg ttgcaatat т ttatcaccag agccgaggcg      2580
cacctgcaag tgtggatccc ccccctcaac attcggggg ccgcgatgc catcatcctc      2640
ctcgcgtgtg tagtccaccc agagctaatc tttgacatca ccaaaaacтccт gctcgccata      2700
ctcggtccgc tcatggtgct ccaggctagc ataactcaag tgccgtactt cgtacgcgcc      2760
caagggctca ttcgtgcatg catgttggtg cggaaggtag ccgggggcca ttatgtccaa      2820
atggcctttg tgaagctgac cgcactgaca ggtacgtacg tttatgacca tctaactcca      2880
ctgcgggact gggcccacgc gggcctgcga gacctcgcgg tggcagtaga gcccgttgtc      2940
ttctctgaca tggagaccaa ggtcatcacc tggggggcag acaccgcagc gtgtggggac      3000
атт atcttgg gtctacctgt ctccgcccga aggggtaggg agata ctt ct ggggccggcc      3060
gatagtcttg aagggcaggg gtggcggctc ctt                                  3093
```

<210> SEQ ID NO 2
<211> LENGTH: 7410
<212> TYPE: DNA
<213> ORGANISM: Hepatitis C virus

<400> SEQUENCE: 2

```
acgcggccgc cgcaaggcaa ctggttcggc tgtacgtgga tgaacggcac tgggttcacc       60
aagacatgcg ggggcccccc gtgtaacatc ggggggggcg gcaataacac cttgacctgc      120
cctacggact gtttccggaa gcaccccgcg gccacttaca caaaatgtgg ttcgggacct      180
tggctgacac ccaggtgctt ggtagactac ccatacaggc tctggcacta cccctgcact      240
gccaacttta ccatcttcaa ggttaggatg tatgtagggg gcgtggagca caggctcgat      300
gctgcatgca att ggacccg aggggaacgt tgcaacttgg aggataggga tagattggag      360
ctcagcccgc tactgctgtc tacaacagag tggcaggtgc tgccctgttc tttcaccacc      420
ctaccggctc tgtccactgg ttt aat tcat ctccatcaga catcgtgga cgtgcaatac      480
ctgtacggta tagggtcggc agttgtttcc tttgcaatca aat gggacta tatcgt gata      540
cttttcctcc tcc ggcgga cgcgcgtctg tgcctgct tgtggatgat gctgctgata      600
gcccaggccg aggccgcctt agaaaaacстg gtggtcctca atgcggcgtc cgtggccgga      660
gcgcatggca ttctctcctt ccttgtgttc tt ctgtgccg cctggtacat caagggcaag      720
ctggtccccg gggcagcata tgctttctat ggaгтатggc cgctgctcct gcttctgctg      780
gccttaccac cacgagctta cgctatggag cgggaгaтgg ctgcatcgtg cggaggcgcg      840
gtgtttgtag gtctggtact cttgactttg tcaccatact атaaagaгтт cctcgccagg      900
ctcatatggt ggttgcaata tttatcacc agagccgaгг cgcacctgca aгтgтgгатc      960
ccccccctca acatt cggгг gгccgcgат gccatcatcc тcстcgcгтг тгтaгтccac     1020
ccaгaгстaa тcтттгacат caccaaaaстc стгстсгсса тaстcггтсс гстcатгггт     1080
стссаггстa гсатaaстса аггссгтас тт сгтасгсг ccсaaгггст сатт сгтгса     1140
```

```
tgcatgttgg tgcggaaggt agccgggggc cattatgtcc aaatggcctt tgtgaagctg    1200
accgcactga caggtacgta cgtttatgac catctaactc cactgcggga ctgggcccac    1260
gcgggcctgc gagacctcgc ggtggcagta gagcccgttg tcttctctga catggagacc    1320
aaggtcatca cctgggggc agacaccgca gcgtgtgggg acattatctt gggtctacct    1380
gtctccgccc gaaggggtag ggagatactt ctggggccgg ccgatagtct tgaagggcag    1440
gggtggcggc tccttgctcc catcacggcc tattcccaac agacgcgggg cctacttggt    1500
tgcatcatca ctagcctcac aggccgggac aaaaaccaag tcgaggggga ggttcaagtg    1560
gtctccaccg cgacacaatc cttcctggcg acctgcgtca atggcgcgtg ctggactgtc    1620
ttccatggtg ccggctcaaa gaccttagct ggcccaaaag gtccaatcac ccagatgtac    1680
actaatgtag acctgaccct cgtcggctgg caggcgcccc ccgggtcgcg ttctctgaca    1740
ccatgcacct gcggcagctc agacctctat ttggtcacga gacatgctga tgtcattccg    1800
gtgcgccggc ggggcgacag tagggggaagc ctactctctc ccagacctgt ctcctacttg    1860
aaaggctcct cgggtggtcc gctgctctgc ccttcgaggc acgctgtggg catcttccgg    1920
gctgctgtgt gcacccgggg ggttgcgaag gcggtggatt tcatacccgt tgaatcaatg    1980
gaaactacta tgcggtctcc ggtcttcacg gataactcat cccccccggc cgtaccgcag    2040
acattccaag tggcccatct acacgcccct actggcagcg gcaagagcac taaggtgccg    2100
gctgcatatg cagcccaagg gtataaggtg ctcgtcctga accgtccgt tgccgctacc    2160 ttgggttttg gggcgtatat gtctaaggca catggtatcg accccaacat cagaactggg    2220
gtaagggcca tcaccacggg cgcccctatt acatactcca cctacggcaa gttccttgcc    2280
gacggcggtt gttccggggg cgcctatgac atcataatat gtgatgagtg ccactcaact    2340
gactcgacta ccatcttggg cattggcaca gtcctggacc aagcggagac ggctggagcg    2400
cggctcgtcg tgctcgccac cgctacgcct ccgggatcgg tcaccgtgcc acaccccaat    2460
attgaggagg tggcccctgtc caacgctgga gaaatcccct tctacggcaa agccatcccc    2520
attgaggtca tcaaggggggg aagacatctc attttctgcc attccaagaa gaagtatgac    2580
gagctcgccg caaagctatc agccctcgga cttaatgctg tagcatatta tcggggtctt    2640
gatgtgtccg tcataccgac caacggagac gtcgttgtcg tggcaacaga cgctctaatg    2700 acgggctta ccgcgacttt tgactcagtg atcgactgta acacatgtgt cacccagaca    2760
gtcgatttca gcctggatcc caccttcacc atcgagacga cgaccgtgcc ccaagacgca    2820
gtggcgcgat cacagcggcg gggtaggact ggtaggggca ggagaggcat ctacaggttt    2880
gtgactccag agaacggcc ctcgggcatg ttcgattcct cggtcctgtg tgagtgctat    2940
gacgcgggct gtgcttggta cgagctcacg cctgctgaga cctcggttag gttgcgggct    3000
tacctgaata caccagggtt gccgtctgc caggaccatc tggagttttg ggagagcgtc    3060
tccacaggcc tcacccacat agatgccat tttctgtccc agactaaaca ggcaggagac    3120 aacttccct acctggtagc ataccaagcc acagtgtgcg ccagagctca agctccacct    3180
ccatcatggg atcaaatgtg gaagtgtctc atacggctca aacccacgct gcacgggcca    3240
acacccctgc tgtataggct aggagccgtc caaaatgaga tcaccctcac acaccccatg    3300
accaaattca tcatggcatg catgtcggct gacctggagg tcgtcactag cacctgggtg    3360
ctagtaggcg gagtccttgc agctctggct gcatattgct tgacaacagg cagtgtggtc    3420
attgtgggta ggatcatctt gtccggggagg ccggctgtta ttcccgacag ggaagtcctc    3480
taccgggagt tcgatgagat ggaagagtgc gcctcacacc tcccttacat cgaacaggga    3540
```

```
atgcagcttg ccgagcaatt caagcagaag gcgctcggat tgctgcaaac agccaccaag    3600
caagcggagc tgctgctccc cgtggtagaa tccaagtggc gagcccttga gaccttctgg    3660
gcgaagcaca tgtggaattt catcagcggg atacagtacc tagcaggctt gtccactctg    3720
cctgggaacc ccgcgatagc atcactgatg gcattcacag cctctatcac cagcccgctc    3780
tccacccaga ataccctatt atttaacatc tggggggat gggtggctgc ccaactcgcc    3840 cccccagtg ctgcttcggc tttcgtgggc gccggtatcg ccggtgcggc tgtcggcagc    3900
ataggtcttg ggaaggtgct tgtggacatc ttggcgggat atggggcagg ggtggctggc    3960
gcgctcgtag cttttaagat catgagcggc gaggtgccct ccaccgagga cctggttaac    4020
ttactccctg ccatcctctc tcccggcgcc ctagtcgtcg gggtcgtgtg cgcagcaata    4080
ctgcgtcggc acgtgggccc gggagagggg gctgtacagt ggatgaaccg gctgatagcg    4140
ttcgcctcgc ggggtaacca cgtttccccc gcgcactatg tgcctgagag cgacgctgcg    4200
gcgcgtgtta ctcagatcct ctccggcctt accatcactc agctgctgaa gaggcttcac    4260
cactggatca atgaggactg ctccacgcca tgctccggtt cgtggctaag ggatgtttgg    4320
gactggatat gcacggtgtt gactgacttc aagacctggc tccagtccaa gctcctgccg    4380
cggttaccgg gggtcccttt cttctcgtgt caacgcgggt acaagggagt ctggcggggg    4440
gacggtatca tgcagaccac ctgcccgtgt ggagcacaga tcaccggaca tgtcaaaaac    4500
ggttccatga ggatcgtcgg gcctaaaacc tgcagcagca cgtggcatgg aacgttcccc    4560
atcaacgcat acaccacagg cccatgcgca ccctccccgg cgccaaacta ttccagggcg    4620
ctatggcggg tggccgctga ggagtacgtg gaggttacgc gggtggggga tttccactac    4680
gtgacgggca tgaccactga caacgtaaag tgcccatgcc aggttccggc ccctgaattc    4740
ttcactgagg tggatggagt gcggttgcac aggtacgctc cggcgtgcaa accctcctt    4800 cgggaggagg tcacattcca ggttgggctc aaccaatacc tggttgggtc acagctccca    4860
tgcgagcccg aaccggatgt agcagtgcta acttccatgc ttaccgaccc ctcccacatc    4920
acagcagaga cggcaaagcg taggctggct aggggtctc ccccctcctt ggccagttct    4980
tcagctagcc agttatctgc gccttccttg aaggcgacat gcactaccca tcatgactcc    5040
ccggacgttg acctcatcga ggccaacctc ctgtggcggc aggagatggg cgggaacatc    5100
acccgcgtgg agtcagagaa taaggtagta attttggact cttccgatcc gctccgagcg    5160
gaggaggacg agagggaacc atccgttgcg gcggagatct tgcggaaaac caagaggttc    5220
cccccggcga tgcccatatg ggcacgcccg gattacaacc ctccgttgct agagtcctgg    5280
aaagacccgg actacgtccc tccggtggta cacgggtgcc cgctaccacc taccaaagct    5340
cctccgatac cacccccacg gagaaagagg acggtagtcc tgacagagtc cactgtgtct    5400
tctgccttgg cggagcttgc tactaagacc tttggcagct ccgggtcgtc ggccgtcgac    5460
agcggcacgg caactgctcc tcccgaccag gcttccgacg acggcgacca aggatctgac    5520
gttgagtcgt attcctccat gccccctctt gagggagagc cggggaccc cgatctcagc    5580 gacgggtctt ggtctaccgt gagcgaggag gccggtgagg acgtcatctg ctgctcaatg    5640
tcctacacat ggacaggcgc cttgatcacg ccatgcgccg cggaggaaag caagttgccc    5700
atcaacccgt tgagcaactc tttgttgcgt caccacaaca tggtctatgc tacaacatcc    5760
cgcagcgcag gcctacggca gaagaaggtc acctttgaca gactgcaagt cctggacgac    5820
cactaccggg acgtgctcaa ggagatgaag gcgaaggcgc cacagttaa ggctaaactc    5880 ctatccatag aagaagcctg taagctgacg cccccacatt cggccagatc caaatttggc    5940
```

```
tatgggcaa aggacgtccg gaacctatcc agcaaggccg ttaaccacat ccgctccgtg    6000
tggaaggact tgctggaaga cactgagaca ccaattgaca ccaccgtcat ggcaaaaagt    6060
gaggttttct gcgtccaacc agagaaagga ggccgcaagc cagctcgcct tatcgtattc    6120
ccagacttgg gggttcgtgt atgcgagaag atggcccttt atgacgtggt ctccacccct    6180
cctcaggccg tgatgggctc ctcatacgga ttccagtact cccctggaca gcgggtcgag    6240
ttcctggtga atgcctggaa atcaaagaaa tgcccctatg gcttttcata tgacacccgc    6300
tgttttgact cgacagtcac tgagagtgac atccgtgttg aggagtcaat ttaccaatgt    6360
tgtgacttgg cccccgaagc cagacaggcc ataaagtcgc tcacagagcg gctttacatt    6420 ggggtcccc tgaccaattc aaaagggcag aactgtggct atcgcggtg ccgcgcgagt    6480 ggcgtgctga cgaccagctg cggtaatacc cttacatgtt acttgaaggc ctctgcagcc    6540
tgtcgagctg caaagctccg ggactgcacg atgctcgtga acggagacga cctcgtcgtc    6600
atctgtgaga gtgcgggaac ccaagaggat gaggcgaacc tacgagtctt cacggaggct    6660
atgactaggt attctgcccc ccccggggac ccgccccgac cagaatacga cttggagcta    6720
ataacatcat gttcctccaa tgtgtcggtc gcgcacgatg catctggcaa aagggtatac    6780
tacctcaccc gcgaccccttc cacccccctt gcacgggctg cgtgggagac agctagacac    6840
actccagtta attcctggct aggcaacatc attatgtatg cgcccaccttt atgggcaagg    6900 atgattctga tgacccattt cttctccatc cttctagccc aggagcaact tgaaaaagcc    6960
ctggattgcc agatctacgg ggcctgttac tccattgagc cacttgacct acctcagatc    7020
attgaacgac tccatggtct tagcgcattt tcactcccata gttactctcc aggtgagatc    7080
aatagggtgg cttcatgcct caggaaactt ggggtaccac ccttgcgagt ctggagacat    7140
cgggccagaa gtgtccgcgc taagctgctg tcccaggggg ggagggctgc cacttgtggt    7200
aagtacctct tcaactgggc agtaaggacc aagctcaaac tcactccaat cccggcagcg    7260
tcccagttgg acttgtccag ctggttcgtg gctggttaca gcgggggaga catatatcac    7320
agcctgtctc gtgcccgacc ccgctggttc atgttgtgcc tactcctact ttcagtaggg    7380
gtaggcatct acctgctccc caaccgataa                                     7410

<210> SEQ ID NO 3
<211> LENGTH: 9048
<212> TYPE: DNA
<213> ORGANISM: Hepatitis C virus

<400> SEQUENCE: 3
cgtagaccgt gcatcatgag cacaaatcct aaaccccaaa gaaaaaccaa acgtaacacc      60
aaccgccgcc cacaggacgt caagttcccg ggtggtggtc agatcgttgg tggagtttac     120
ctgttgccgc gcaggggccc caggttgggt gtgcgcgcga ctaggaagac ttccgagcgg     180
tcacaacctc gtggaaggcg acaacctatc cccaaggctc gccagcccga ggcagggcc     240 tgggctcagc ccgggtaccc cttggcccctc tatggcaacg agggcatggg gtgggcagga     300
tggctcctgt caccccgcgg ctcccggcct agttggggcc ccacggaccc ccggcgtagg     360
tcgcgtaatt tgggtaaggt catcgatacc ctcacatgcg gcttcgccga cctcatgggg     420
tacattccgc tcgtcggcgc cccctaggg ggcgttgcca gggccctggc acatggtgtc     480
cgggttgtgg aggacggcgt gaactatgca acagggaatt tgcccggttg ctctttctct     540
atcttcctct tggctctgct gtcctgtttg accatcccag cttccgctta tgaggtgcgc     600
aacgtatccg ggatatacca tgtcacgaac gactgctcca actcaagtat tgtgtatgag     660
```

```
gcagcggaca tgatcatgca taccccgggg tgcgtgccct gcgttcggga gggcaactcc    720
tcccgttgct gggtggcact tactcccacg ctagcggcca ggaatgccag cgtccccact    780
acggcaatac gacgccatgt cgatttgctc gttggggcgg ctgctttctg ctccgctatg    840
tatgtgggag atctctgcgg atctgttttc cttgtctccc agctgttcac cttctcgccc    900
cgccggcatg agacaataca ggactgcaat tgctcaatct atcccggcca cgtgtcaggt    960
caccgcatgg cttgggacat gatgatgaac tggtcgccta caacgccct ggtggtgtcg   1020 cagttactcc ggatcccaca agctatcgtg gacatggtgg cggggggctca ctgggtgtc   1080 ctagcgggcc ttgcctacta ttccatggtg gggaactggg ctaaggtatt gattgtgatg   1140
ctactttttg ccggcgtcga cggggagacc cgtgtgacag gggggcagat agccagaaat   1200
gcctactcgc tcacgaccct cttttcatct gggtcggctc agaacatcca gctcataaac   1260
accaacggta gctggcacat caacaggact gccctgaact gcaatgactc cctcaacacc   1320
gggtttcttg ccgcgctgtt ctacacgcac aagttcaacg cgtccggatg tccagagcgc   1380
ttggccagct gccgcccat tgacaagttc gatcaggggt ggggtcccat cacttatgct   1440
gagcagggcg ccaggacca gaggccttat tgctggcact acgcacctaa accatgtggt   1500
attgtatccg cgtcgaaggt gtgtggtcca gtgtattgtt tcaccccaag cccagttgta   1560
gtggggacga ccgatcggtt cggtgtccct acgtatagct ggggggagaa tgagacagac   1620
gtgctgctcc ttaacaacac gcggccgccg caaggcaact ggttcggctg tacgtggatg   1680
aacggcactg ggttcaccaa gacatgcggg ggcccccgt gtaacatcgg ggggggcggc   1740 aataacaccct tgacctgccc tacgactgt ttccggaagc accccgcggc cacttacaca   1800
aaatgtggtt cgggaccttg gctgacaccc aggtgcttgg tagactaccc atacaggctc   1860
tggcactacc cctgcactgc caactttacc atcttcaagg ttaggatgta tgtaggggggc   1920 gtggagcaca ggctcgatgc tgcatgcaat tggacccgag gggaacgttg caacttggag   1980
gatagggata gattggagct cagcccgcta ctgctgtcta caacagagtg gcaggtgctg   2040
ccctgttctt tcaccaccct accggctctg tccactggtt taattcatct ccatcagaac   2100
atcgtggacg tgcaataccc tgtacggtata gggtcggcag ttgtttcctt tgcaatcaaa   2160
tgggactata tcgtgatact tttcctcctc ctggcggacg cgcgcgtctg tgcctgcttg   2220
tggatgatgc tgctgatagc ccaggccgag gccgccttag aaaacctggt ggtcctcaat   2280
gcggcgtccg tggccggagc gcatggcatt ctctccttcc ttgtgttctt ctgtgccgcc   2340
tggtacatca agggcaagct ggtcccgggg gcagcatatg cttctatgg agtatggccg   2400 ctgctcctgc ttctgctggc cttaccacca cgagcttacg ctatggagcg ggagatggct   2460
gcatcgtgcg gaggcgcggt gtttgtaggt ctggtactct tgactttgtc accatactat   2520
aaagagttcc tcgccaggct catatggtgg ttgcaatatt ttatcaccag agccgaggcg   2580
cacctgcaag tgtggatccc cccctcaac attcggggg gccgcgatgc catcatcctc   2640
ctcgcgtgtg tagtccaccc agagctaatc tttgacatca ccaaactcct gctcgccata   2700
ctcggtccgc tcatggtgct ccaggctagc ataactcaag tgccgtactt cgtacgcgcc   2760
caagggctca ttcgtgcatg catgttggtg cggaaggtag ccgggggcca ttatgtccaa   2820
atggcctttg tgaagctgac cgcactgaca ggtacgtacg tttatgacca tctaactcca   2880
ctgcgggact gggcccacgc gggcctgcga gacctcgcgg tggcagtaga gcccgttgtc   2940
ttctctgaca tggagaccaa ggtcatcacc tggggggcag acaccgcagc gtgtgggac   3000 attatcttgg gtctacctgt ctccgcccga aggggtaggg agatacttct ggggccggcc   3060
```

```
gatagtcttg aagggcaggg gtggcggctc cttgctccca tcacggccta ttcccaacag   3120
acgcggggcc tacttggttg catcatcact agcctcacag gccgggacaa aaaccaagtc   3180
gagggggagg ttcaagtggt ctccaccgcg acacaatcct tcctggcgac ctgcgtcaat   3240
ggcgcgtgct ggactgtctt ccatggtgcc ggctcaaaga ccttagctgg cccaaaaggt   3300
ccaatcaccc agatgtacac taatgtagac ctggacctcg tcggctggca ggcgcccccc   3360
gggtcgcgtt ctctgacacc atgcacctgc ggcagctcag acctctattt ggtcacgaga   3420
catgctgatg tcattccggt gcgccggcgg ggcgacagta ggggaagcct actctctccc   3480
agacctgtct cctacttgaa aggctcctcg ggtggtccgc tgctctgccc ttcgaggcac   3540
gctgtgggca tcttccgggc tgctgtgtgc acccgggggg ttgcgaaggc ggtggatttc   3600
atacccgttg aatcaatgga aactactatg cggtctccgg tcttcacgga taactcatcc   3660
cccccggccg taccgcagac attccaagtg gcccatctac acgccctac tggcagcggc    3720 aagagcacta aggtgccggc tgcatatgca gcccaagggt ataaggtgct cgtcctgaac   3780
ccgtccgttg ccgctacctt gggttttggg gcgtatatgt ctaaggcaca tggtatcgac   3840
cccaacatca gaactggggt aagggccatc accacgggcg cccctattac atactccacc   3900
tacggcaagt tccttgccga cggcggttgt tccgggggcg cctatgacat cataatatgt   3960
gatgagtgcc actcaactga ctcgactacc atcttgggca ttggcacagt cctggaccaa   4020
gcggagacgc tggagcgcg gctcgtcgtg ctcgccaccg ctacgcctcc gggatcggtc    4080
accgtgccac accccaatat tgaggaggtg gccctgtcca acgctggaga atccccttc    4140 tacggcaaag ccatccccat tgaggtcatc aaggggggaa gacatctcat tttctgccat   4200
tccaagaaga agtatgacga gctcgccgca aagctatcag ccctcggact taatgctgta   4260
gcatattatc ggggtcttga tgtgtccgtc ataccgacca acgagacgt cgttgtcgtg    4320 gcaacagacg ctctaatgac gggctttacc ggcgactttg actcagtgat cgactgtaac   4380
acatgtgtca cccagacagt cgatttcagc ctggatccca ccttcaccat cgagacgacg   4440
accgtgcccc aagacgcagt ggcgcgatca cagcggcggg gtaggactgg taggggcagg   4500
agaggcatct acaggtttgt gactccagga gaacggccct cgggcatgtt cgattcctcg   4560
gtcctgtgtg agtgctatga cgcgggctgt gcttggtacg agctcacgcc tgctgagacc   4620
tcggttaggt tgcgggctta cctgaataca ccagggttgc ccgtctgcca ggaccatctg   4680
gagttttggg agagcgtctc cacaggcctc acccacatag atgcccattt tctgtcccag   4740
actaaacagg caggagacaa cttcccctac ctggtagcat accaagccac agtgtgcgcc   4800
agagctcaag ctccacctcc atcatgggat caaatgtgga agtgtctcat acggctcaaa   4860
cccacgctgc acgggccaac accctgctg tataggctag gagccgtcca aaatgagatc    4920
accctcacac accccatgac caaattcatc atggcatgca tgtcggctga cctggaggtc   4980
gtcactagca cctgggtgct agtaggcgga gtccttgcag ctctggctgc atattgcttg   5040
acaacaggca gtgtggtcat tgtgggtagg atcatcttgt ccgggaggcc ggctgttatt   5100
cccgacaggg aagtcctcta ccgggagttc gatgagatgg aagagtgcgc ctcacacctc   5160
ccttacatcg aacagggaat gcagcttgcc gagcaattca gcagaaggc gctcggattg    5220 ctgcaaacag ccaccaagca gcggaggct gctgctcccg tggtagaatc caagtggcga    5280
gcccttgaga ccttctgggc gaagcacatg tggaatttca tcagcgggat acagtaccta   5340
gcaggcttgt ccactctgcc tgggaacccc gcgatagcat cactgatggc attcacagcc   5400
tctatcacca gcccgctctc cacccagaat accctattat ttaacatctg gggggatgg   5460
```

```
gtggctgccc aactcgcccc ccccagtgct gcttcggctt tcgtgggcgc cggtatcgcc    5520
ggtgcggctg tcggcagcat aggtcttggg aaggtgcttg tggacatctt ggcgggatat    5580
ggggcagggg tggctggcgc gctcgtagct tttaagatca tgagcggcga ggtgccctcc    5640
accgaggacc tggttaactt actccctgcc atcctctctc ccggcgccct agtcgtcggg    5700
gtcgtgtgcg cagcaatact gcgtcggcac gtgggcccgg gagaggggc tgtacagtgg     5760 atgaaccggc tgatagcgtt cgcctcgcgg ggtaaccacg tttcccccgc gcactatgtg    5820
cctgagagcg acgctgcggc gcgtgttact cagatcctct ccggccttac catcactcag    5880
ctgctgaaga ggcttcacca ctggatcaat gaggactgct ccacgccatg ctccggttcg    5940
tggctaaggg atgtttggga ctggatatgc acggtgttga ctgacttcaa gacctggctc    6000
cagtccaagc tcctgccgcg gttaccgggg gtccctttct tctcgtgtca acgcgggtac    6060
aagggagtct ggcggggga cggtatcatg cagaccacct gcccgtgtgg agcacagatc     6120
accggacatg tcaaaaacgg ttccatgagg atcgtcgggc taaaacctg cagcagcacg     6180 tggcatggaa cgttccccat caacgcatac accacaggcc catgcgcacc ctccccggcg    6240
ccaaactatt ccagggcgct atggcgggtg gccgctgagg agtacgtgga ggttacgcgg    6300
gtgggggatt tccactacgt gacgggcatg accactgaca acgtaaagtg cccatgccag    6360
gttccggccc ctgaattctt cactgaggtg gatggagtgc ggttgcacag gtacgctccg    6420
gcgtgcaaac ccctcctacg ggaggaggtc acattccagg ttgggctcaa ccaatacctg    6480
gttgggtcac agctcccatg cgagcccgaa ccggatgtag cagtgctaac ttccatgctt    6540
accgacccct cccacatcac agcagagacg gcaaagcgta ggctggctag ggggtctccc    6600
ccctccttgg ccagttcttc agctagccag ttatctgcgc cttccttgaa ggcgacatgc    6660
actacccatc atgactcccc ggacgttgac ctcatcgagg ccaacctcct gtggcggcag    6720
gagatgggcg ggaacatcac ccgcgtggag tcagagaata aggtagtaat tttggactct    6780
ttcgatccgc tccagcggag ggaggacgag agggaaccat ccgttgcggc ggagatcttg    6840
cggaaaacca agaggttccc cccggcgatg cccatatggg cacgcccgga ttacaaccct    6900
ccgttgctag agtcctggaa agacccggac tacgtccctc cggtggtaca cgggtgcccg    6960
ctaccaccta ccaaagctcc tccgatacca cccccacgga gaaagaggac ggtagtcctg    7020
acagagtcca ctgtgtcttc tgccttggcg gagcttgcta ctaagacctt tggcagctcc    7080
gggtcgtcgg ccgtcgacag cggcacggca actgctcctc ccgaccaggc ttccgacgac    7140
ggcgaccaag gatctgacgt tgagtcgtat tcctccatgc cccctcttga gggagagccg    7200 ggggacccg atctcagcga cgggtcttgg tctaccgtga gcgaggaggc cggtgaggac    7260
gtcatctgct gctcaatgtc ctacacatgg acaggcgcct tgatcacgcc atgcgccgcg    7320
gaggaaagca agttgcccat caacccgttg agcaactctt gttgcgtca ccacaacatg    7380 gtctatgcta caacatcccg cagcgcaggc ctacggcaga agaaggtcac ctttgacaga    7440
ctgcaagtcc tggacgacca ctaccggac gtgctcaagg atgaaggc gaaggcgtcc     7500 acagttaagg ctaaactcct atccatagaa gaagcctgta agctgacgcc cccacattcg    7560
gccagatcca aatttggcta tgggcaaag gacgtccgga acctatccag caaggccgtt    7620
aaccacatcc gctccgtgtg gaaggacttg ctggaagaca ctgagacacc aattgacacc    7680
accgtcatgg caaaaagtga ggttttctgc gtccaaccag agaaggagg ccgcaagcca    7740 gctcgcctta tcgtattccc agacttgggg gttcgtgtat gcgagaagat ggccctttat    7800
gacgtggtct ccaccctccc tcaggccgtg atgggctcct catacggatt ccagtactcc    7860
```

```
cctggacagc gggtcgagtt cctggtgaat gcctggaaat caaagaaatg ccctatgggc    7920
ttttcatatg acacccgctg ttttgactcg acagtcactg agagtgacat ccgtgttgag    7980
gagtcaattt accaatgttg tgacttggcc cccgaagcca gacaggccat aaagtcgctc    8040
acagagcggc tttacattgg gggtcccctg accaattcaa aagggcagaa ctgtggctat    8100
cgccggtgcc gcgcgagtgg cgtgctgacg accagctgcg gtaataccct tacatgttac    8160
ttgaaggcct ctgcagcctg tcgagctgca aagctccggg actgcacgat gctcgtgaac    8220
ggagacgacc tcgtcgtcat ctgtgagagt gcgggaaccc aagaggatga ggcgaaccta    8280
cgagtcttca cggaggctat gactaggtat tctgcccccc ccggggaccc gccccgacca    8340
gaatacgact tggagctaat aacatcatgt tcctccaatg tgtcggtcgc gcacgatgca    8400
tctggcaaaa gggtatacta cctcacccgc gacccctcca ccccccttgc acgggctgcg    8460
tgggagacag ctagacacac tccagttaat tcctggctag caacatcat tatgtatgcg    8520
cccaccttat gggcaaggat gattctgatg acccatttct tctccatcct tctagcccag    8580
gagcaacttg aaaaagccct ggattgccag atctacgggg cctgttactc cattgagcca    8640
cttgacctac ctcagatcat tgaacgactc catggtctta gcgcattttc actccatagt    8700
tactctccag gtgagatcaa tagggtggct tcatgcctca ggaaacttgg ggtaccaccc    8760
ttgcgagtct ggagacatcg ggccagaagt gtccgcgcta agctgctgtc caggggggg    8820
agggctgcca cttgtggtaa gtacctcttc aactgggcag taaggaccaa gctcaaactc    8880
actccaatcc cggcagcgtc ccagttggac ttgtccagct ggttcgtggc tggttacagc    8940
ggggagaca tatatcacag cctgtctcgt gcccgacccc gctggttcat gttgtgccta    9000
ctcctacttt cagtagggt aggcatctac ctgctcccca accgataa                 9048

<210> SEQ ID NO 4
<211> LENGTH: 849
<212> TYPE: DNA
<213> ORGANISM: Vaccinia virus

<400> SEQUENCE: 4
gatgatgatg atgatgatga tgatgatgat gtcatagacg atgatgatta taatccaaaa      60
cccactccga taccggagcc tcaccctaga ccaccgtttc ccagacatga atatcataag     120
aggccgaaag ttcttcctgt agaagaacct gatcctgtca aaaagacgc ggatcgtata     180
agacttgata atcatatatt aaacacattg gatcataatc ttaattccat cggacactat     240
tgttgtgata cagcagcagt tgataggtta gaacatcaca ttgaaacatt gggacaatat     300
gcagtaatac tagcaagaaa gataaatatg caaacattac tgttcccatg gccattacct     360
actgtccatc cacatgcgat agatggtagt attccgccac atgggagatc tacgatctta     420
taattacacg attgtagtta agttttgaat aaaatttttt tataataaat agaggtcacg     480
aacctcgact ctagaggatc ccattgtgaa aaattgaaaa actagtctaa tttattgcac     540
ggtgtgaaaa attgaaaaac tagtctaatt tattgcacgg tgtgaaaaat tgaaaaacta     600
gtctaattta ttgcacggtg tgaaaaattg aaaaactagt ctaatttatt gcacggtgtg     660
aaaaattgaa aaactagtct aatttattgc acggtgtgaa aaattgaaaa actagtctaa     720
tttattgcac ggtgtgaaaa attgaaaaac tagtctaatt tattgcacgg tgtgaaaaat     780
tgaaaaacta gtctaattta ttgcacggtg tgaaaaattg aaaaactagt taatttattg     840
cacggtgtg                                                             849
```